United States Patent
Tobimatsu et al.

(10) Patent No.: US 11,169,057 B2
(45) Date of Patent: Nov. 9, 2021

(54) PARTICLE DISPERSION DEVICE AND PARTICLE DISPERSION METHOD

(71) Applicant: SYSMEX CORPORATION, Kobe (JP)

(72) Inventors: Hiroaki Tobimatsu, Kobe (JP); Toshimi Sato, Kobe (JP)

(73) Assignee: Sysmex Corporation, Hyogo (JP)

( * ) Notice: Subject to any disclaimer, the term of this patent is extended or adjusted under 35 U.S.C. 154(b) by 422 days.

(21) Appl. No.: 15/825,992

(22) Filed: Nov. 29, 2017

(65) Prior Publication Data

US 2018/0149564 A1   May 31, 2018

(30) Foreign Application Priority Data

Nov. 30, 2016   (JP) .............................. JP2016-232022

(51) Int. Cl.
   *G01N 1/38*      (2006.01)
   *C12Q 1/68*      (2018.01)
   (Continued)

(52) U.S. Cl.
   CPC ............. *G01N 1/38* (2013.01); *B01F 1/0022* (2013.01); *B01F 5/025* (2013.01); *B01F 5/0237* (2013.01);
   (Continued)

(58) Field of Classification Search
   CPC .... G01N 1/38; G01N 35/1011; G01N 35/109; B01F 1/0022; B01F 5/0237; B01F 5/025;
   (Continued)

(56) References Cited

U.S. PATENT DOCUMENTS

| 5,105,842 A | 4/1992 | Wells |
| 5,482,863 A | 1/1996 | Knobel |

(Continued)

FOREIGN PATENT DOCUMENTS

| CN | 103861669 A | 6/2014 |
| JP | H04-328467 A | 11/1992 |

(Continued)

OTHER PUBLICATIONS

Berensmeier, S. (2006). "Magnetic particles for the separation and purification of nucleic acids." Appl Microbiol Biotechnol. 73:495-504. (Year: 2006).*

(Continued)

*Primary Examiner* — Matthew D Krcha
*Assistant Examiner* — Jacqueline Brazin
(74) *Attorney, Agent, or Firm* — Crowell & Moring LLP

(57) ABSTRACT

A particle dispersion method for dispersing particles (500) fixed on the inner surface of a container (12) into a liquid. The particle dispersion method includes a discharge step of discharging a liquid into the container (12). The container (12) has a cylindrical main body part (310), and an inclined part (311) having an inner diameter that decreases from the main body part (310) side to the bottom part side and having a constant angle relative to the central axis of the container. In the discharge step, the liquid is discharged from above the inclined part (311) toward the inclined part (311) on the side opposite the particles (500) fixed to the inner surface of the container (12) across the central axis (300) of the container (12).

17 Claims, 29 Drawing Sheets

(51) Int. Cl.
    *G01N 35/10*     (2006.01)
    *C12N 15/10*     (2006.01)
    *B01F 5/02*     (2006.01)
    *B01F 1/00*     (2006.01)
    *C12Q 1/6806*     (2018.01)
    *C12Q 1/6844*     (2018.01)
    *G01N 35/00*     (2006.01)
    *B01L 7/00*     (2006.01)

(52) U.S. Cl.
    CPC ....... *C12N 15/1013* (2013.01); *C12Q 1/6806* (2013.01); *C12Q 1/6844* (2013.01); *G01N 35/109* (2013.01); *G01N 35/1011* (2013.01); *B01L 7/52* (2013.01); *G01N 35/0098* (2013.01); *G01N 2035/00544* (2013.01); *G01N 2035/00574* (2013.01); *G01N 2035/106* (2013.01)

(58) Field of Classification Search
    CPC . C12N 15/1013; C12Q 1/6806; C12Q 1/6844
    USPC .......................................................... 436/94
    See application file for complete search history.

(56) References Cited

U.S. PATENT DOCUMENTS

| | | | |
|---|---|---|---|
| 5,482,864 A | 1/1996 | Knobel | |
| 8,993,345 B2* | 3/2015 | Aizawa | G01N 33/54346 436/172 |
| 2002/0012916 A1* | 1/2002 | Gundling | B01L 7/52 435/6.19 |
| 2008/0240988 A1* | 10/2008 | Wakamiya | G01N 35/00693 422/68.1 |
| 2010/0203573 A1* | 8/2010 | Heinonen | G01N 35/028 435/29 |
| 2011/0009608 A1* | 1/2011 | Kim | C12N 15/1013 536/25.41 |
| 2011/0104028 A1* | 5/2011 | Kuan | B01L 3/5085 422/608 |
| 2013/0130369 A1* | 5/2013 | Wilson | G16B 99/00 435/289.1 |
| 2014/0170026 A1* | 6/2014 | Uno | G01N 35/1011 422/82.05 |
| 2015/0346230 A1* | 12/2015 | Setomaru | G01N 35/02 422/64 |
| 2016/0238620 A1 | 8/2016 | Shimamori et al. | |

FOREIGN PATENT DOCUMENTS

| | | |
|---|---|---|
| JP | H07-174763 A | 7/1995 |
| JP | H10-96732 A | 4/1998 |
| JP | 2003-530087 A | 10/2003 |
| JP | 2004-500014 A | 1/2004 |
| JP | 2008-249576 A | 10/2008 |
| TW | I429475 B | 3/2014 |
| WO | 2015/079829 A1 | 6/2015 |
| WO | 2016/043291 A1 | 3/2016 |

OTHER PUBLICATIONS

The Communication pursuant to Article 94(3) EPC dated Jul. 17, 2019 in a counterpart European patent application No. 17204622.9.
The Japanese Office Action dated Nov. 4, 2020 in a counterpart Japanese patent application No. 2016-232022.
Chinese Office Action dated Sep. 3, 2021 in a counterpart Chinese patent application No. 201711229086.5.

* cited by examiner

Tapered bottom container

*Solution Time 0.01 (s)*

Ellipsoidal bottom container

*Solution Time 0.01 (s)*

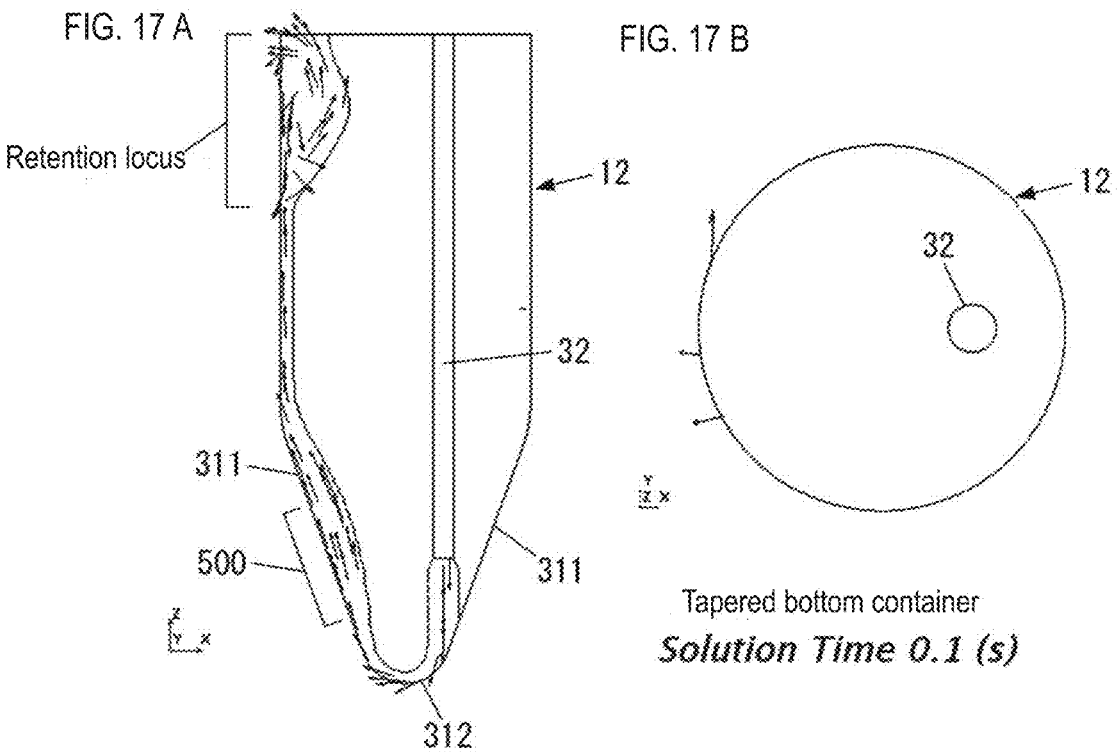
FIG. 17 A
FIG. 17 B
Tapered bottom container
Solution Time 0.1 (s)
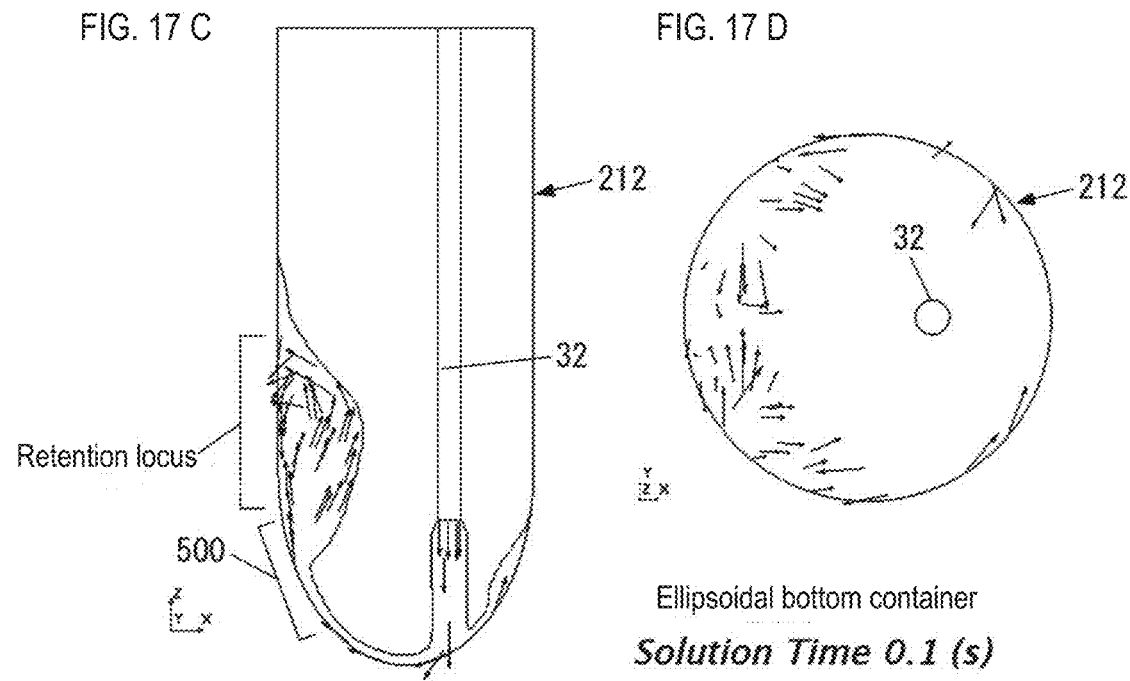
FIG. 17 C
FIG. 17 D
Ellipsoidal bottom container
Solution Time 0.1 (s)

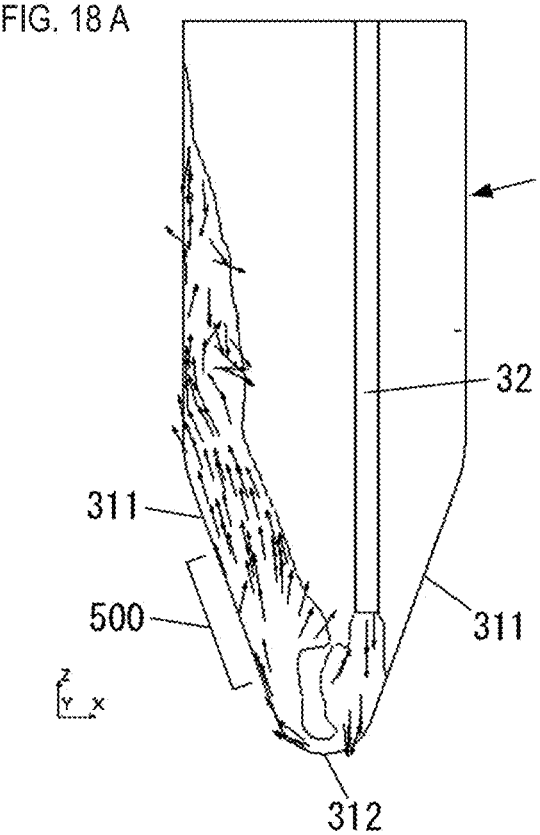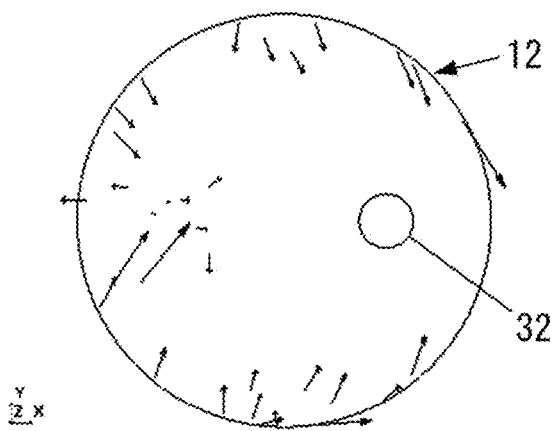
FIG. 18 A
FIG. 18 B
Tapered bottom container
*Solution Time 0.214 (s)*
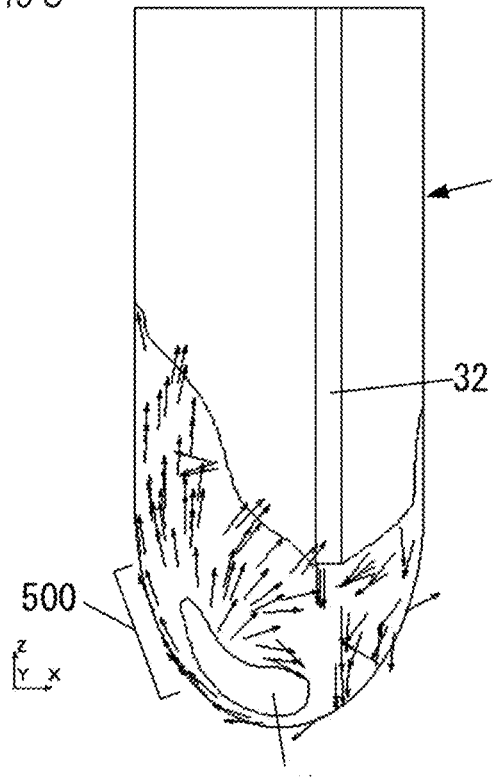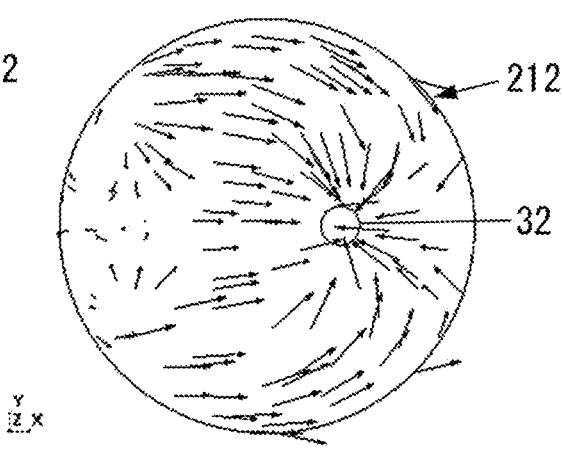
FIG. 18 C
FIG. 18 D
Ellipsoidal bottom container
*Solution Time 0.205 (s)*

Tapered bottom container
*Solution Time 0.45 (s)*

Ellipsoidal bottom container
*Solution Time 0.45 (s)*

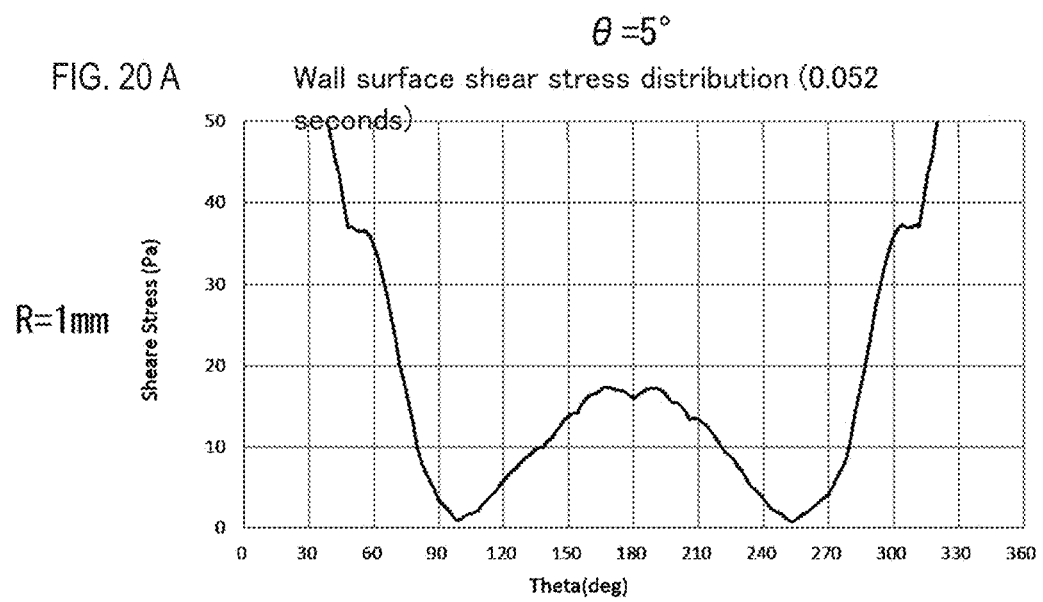
FIG. 20 A Wall surface shear stress distribution (0.052 seconds), θ=5°, R=1mm
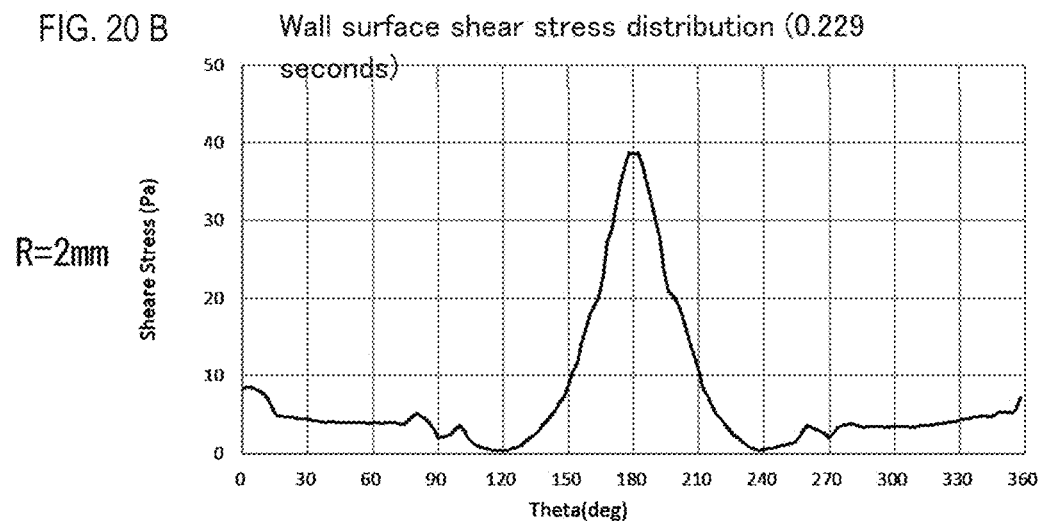
FIG. 20 B Wall surface shear stress distribution (0.229 seconds), R=2mm X=1.2mm
Tapered bottom
(θ=20°)
(R=1.75mm)

Ellipsoidal bottom

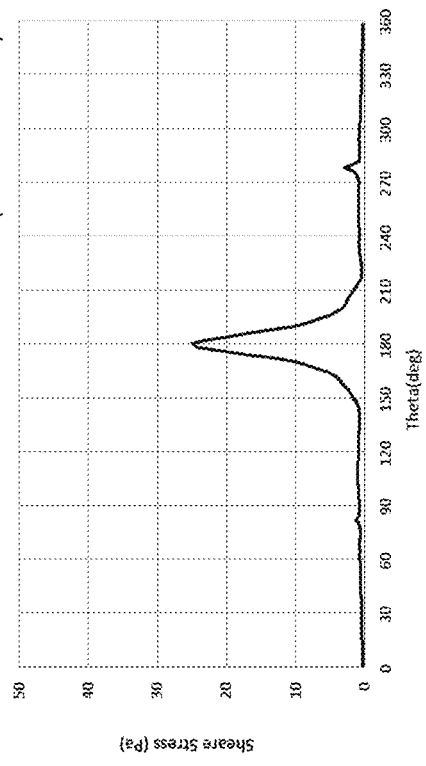
FIG. 27 A  Tapered bottom ($\theta=20°$, R=1.75mm), X=1.5mm, Wall surface shear stress distribution (0.213 seconds)
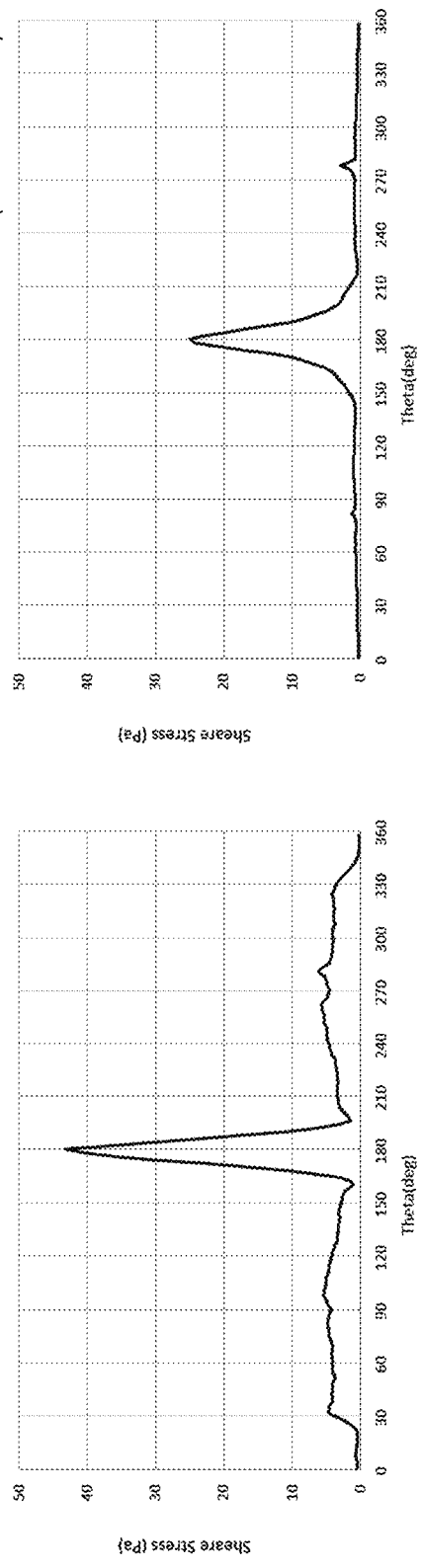
FIG. 27 B  Shear stress maximum value transition
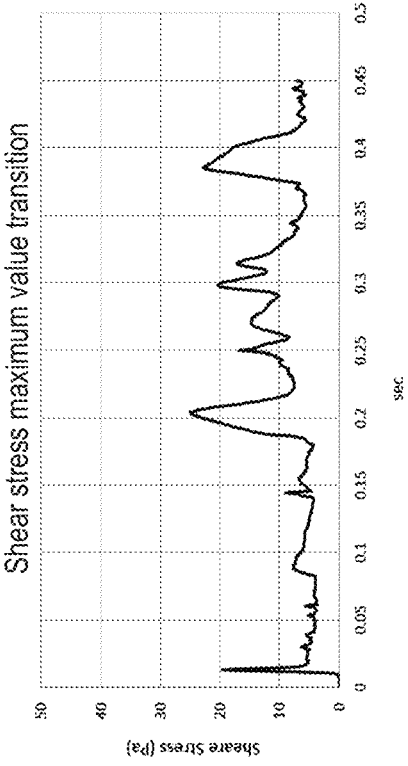
FIG. 27 C  Ellipsoidal bottom, Wall surface shear stress distribution (0.203 seconds)
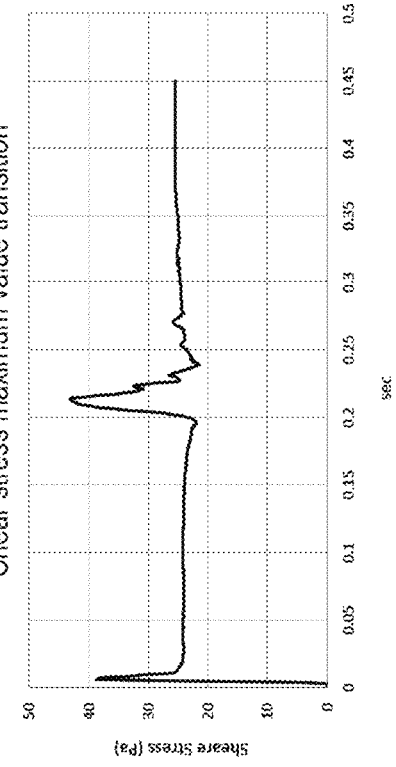
FIG. 27 D  Shear stress maximum value transition

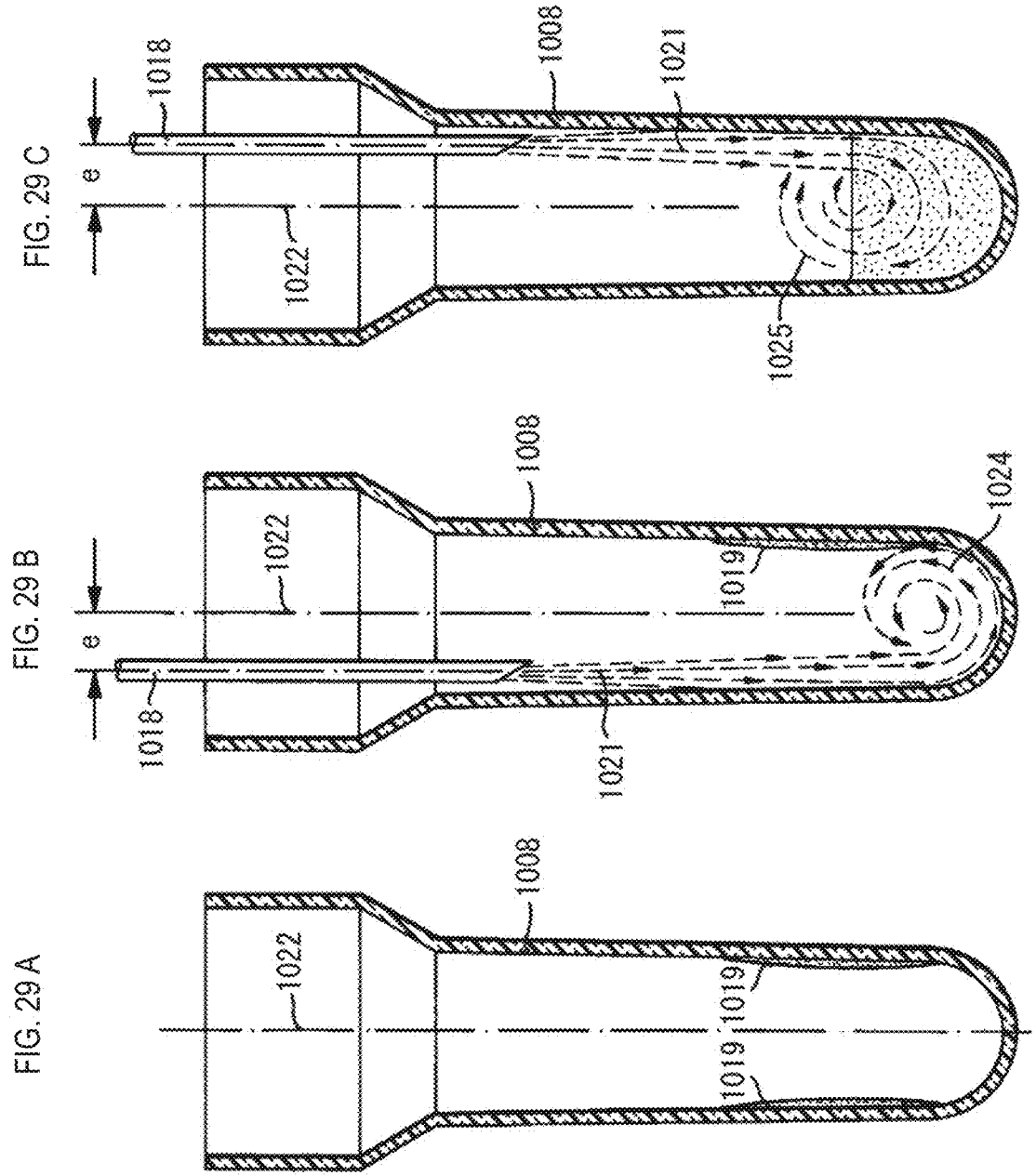

PARTICLE DISPERSION DEVICE AND PARTICLE DISPERSION METHOD

RELATED APPLICATIONS

This application claims priority from prior Japanese Patent Application Publication No. 2016-232022, filed on Nov. 30, 2016, entitled "PARTICLE DISPERSION DEVICE AND PARTICLE DISPERSION METHOD," the entire contents of which are incorporated herein by reference.

BACKGROUND OF THE INVENTION

1. Field of the Invention

The invention relates to a particle dispersion device and particle dispersion method.

2. Description of the Related Art

For example, in order to obtain a substance to be measured from a sample such as blood, there is a known method in which a substance to be measured is fixed to the inner surface of a container and subjected to solid-liquid separation. Solid-liquid separation is performed, for example, to remove excess culture fluid from the cell dispersion. Solid-liquid separation also is performed to separate magnetic particles bound to a substance to be measured such as a nucleic acid and an antigen from other contaminants or the like in a genetic test or an immunological test.

In the case of solid-liquid separation, it is necessary to again disperse the measurement target substance adhered to the inner surface of the container into the liquid in order to carry out the analysis of the next step.

Here, Japanese Patent Application Publication No. H07-174763 discloses a method of dispersing a measurement target substance (particles 1019) adhered to a reaction vessel 1008 by introducing a reagent solution 1021 into the reaction vessel 1008 to form vortices 1024 and 1025 in the reaction vessel 1008, as shown in FIG. 29. In the method disclosed in Japanese Patent Application Publication No. H07-174763, a pipette needle 1018 at a first position with a first predetermined distance e from the central longitudinal axis 1022 of the reaction vessel 1008 moves the reagent solution 1021 forms a vortex within the reaction vessel 1008 when a reagent 1021 is introduced into the reaction vessel 1008, as shown in FIG. 29B. As shown in FIG. 29C, a pipette needle 1018 at a second position with a second predetermined distance e from the central longitudinal axis 1022 of the reaction vessel 1008 also forms a vortex in the opposite direction within the reaction vessel 1008 when the reagent 1021 is introduced into the reaction vessel 1008.

However, for example, when a nucleic acid extracted from a cell is the measurement target substance, magnetic particles as small as about 1 µm are adhered to the nucleic acid, and once fixed may be difficult to disperse again. Since nucleic acids are usually highly polar and easily soluble in water, the nucleic acid also may be dispersed in an organic solvent such as ethanol when solid-liquid separation of nucleic acids is performed. Since the nucleic acid is barely soluble in organic solvent, it may be difficult to re-disperse the nucleic acid in the organic solvent once the nucleic acid is fixed on the inner surface of the container. For this reason, the measurement target substance is not adequately dispersed in the liquid, and considerable time is required for the dispersion operation. Hence, there is a need for a technique that can re-disperse the particles that are fixed to a container more efficiently into a liquid.

SUMMARY OF THE INVENTION

One aspect of the invention is a particle dispersion method for dispersing particles (500) fixed on the inner surface of a container (12) into a liquid. In the embodiment, the particle dispersion method includes a discharge step of discharging a liquid into the container (12). The container (12) has a cylindrical main body part (310), and an inclined part (311) having an inner diameter that decreases from the main body part (310) side to the bottom part side and having a constant angle relative to the central axis of the container. In the discharge step, the liquid is discharged from above the inclined part (311) toward the inclined part (311) on the side opposite the particles (500) fixed to the inner surface of the container (12) across the central axis (300) of the container (12). By discharging the liquid in this way a strong shear stress can be stably applied to the particles fixed to the inner surface of the container. Particles can be efficiently dispersed in the container by strong and stable shear stress.

In the embodiment, the particle dispersion method also includes a suction step of suctioning the liquid in the container (12), and the discharge step can be performed after the suction step. By suctioning the liquid and then discharging the liquid, it is possible to more efficiently disperse the particles in the container.

In the suction step, suction of the liquid is preferably performed until the particles (500) fixed to the inner surface of the container (12) are exposed from the liquid surface of the liquid. By discharging the liquid when the particles are exposed from the liquid surface, it is possible to more efficiently disperse the particles in the container.

After the discharge step, a second discharge step of suctioning the liquid in the container (12) and thereafter discharging the liquid at a second discharge position different from the discharge position of the prior discharge step on the inclined part (311) on the opposite side of the particles (500) fixed to the inner surface of the container (12) with the central axis (300) of the container (12) interposed therebetween. By discharging from different positions, it is possible to more efficiently disperse the particles in the container.

The discharge position in the discharge step and the second discharge position in the second discharge step are preferably different in the circumferential direction of the container (12). Discharge from different positions in the circumferential direction makes it possible to disperse the particles in the container even if the fixing range of the particles spreads in the circumferential direction.

The discharge position in the discharge step is preferably above the suction position in the suction step. Since the position of the nozzle when suctioning the liquid is preferably as low as possible in order to suction more liquid but need not be downward at the time of discharge, the discharge can be performed at an appropriate position above the position when the liquid is suctioned.

In the suction step, the liquid is preferably suctioned on the central axis (300) of the container (12). Since the center position of the container is the deepest, more liquid can be suctioned.

In the suction step, liquid also may be suctioned on the inclined part (311) on the side opposite the particles (500) fixed to the inner surface of the container (12) across the central axis (300) of the container (12). In this case, the movement distance of the nozzle between suction and discharge of the nozzle can be shortened.

The discharge position in the discharge step is preferably a position where the tip of the nozzle (32) for discharging the liquid is immersed in the discharged liquid. In this case, it is preferable to use the entire amount of discharged liquid for particle dispersion.

The container (12) preferably also includes a bottom part (312) having a rounded shape. When the bottom part has a rounded shape, the liquid flow from the position where the liquid first strikes the container to the position of the particles is easily stabilized.

The roundness of the bottom part (312) is preferably such that the radius of curvature of the circle that contacts an arbitrary point in the roundness is 1 mm or more and 3 mm or less, and more preferably the radius of curvature of a circle that contacts an arbitrary point in the roundness is 1 mm or more and 2 mm or less. As a result, the magnitude and the stability of the shear stress acting on the particles fixed to the inner surface of the container are improved.

The angle of the inclined part (311) of the container (12) relative to the central axis (300) of the container (12) is preferably 5° or more and 60° or less, and the angle of the inclination part (311) relative to the central axis (300) of the container (12) is more preferably 10° or more and 45° or less. As a result, the magnitude and the stability of the shear stress are improved.

The particles (500) preferably include magnetic particles. Since the magnetic particles tend to firmly adhere to each other, it is possible to stably perform particle dispersion by vigorously applying a strong shearing stress to the particles. The particles (500) preferably include magnetic particles that have adhered nucleic acid. Particles (500) fixed on the inner surface of the container (12) are preferably magnetic particles (500) with adhered nucleic acid aggregated by magnetic force. It is particularly necessary that a strong shearing stress is stably enacted Since the magnetic particles having fixed nucleic acid aggregated by magnetic force are firmly adhered to each other.

The liquid preferably includes an organic solvent. Although dispersion of the particles may become difficult when the liquid includes an organic solvent, the particles can be reliably dispersed if a strong shear stress is stably applied to the particles. The liquid preferably includes ethanol. Although dispersion of the particles may become difficult when the liquid includes ethanol, the particles can be reliably dispersed if a strong shear stress is stably applied to the particles.

Another aspect of the invention is a particle dispersion device. The particle dispersion device of the embodiment includes a setting part (110) configured to be installed a container (12) which has a cylindrical main body part (310) and an inclined part (311) having an inner diameter that decreases from the main body part (310) side toward the bottom part side and having an angle relative to the central axis of the container is constant, a nozzle (32) configured to discharge a liquid into the container (12), and a control unit (405) configured to control the nozzle (32) so as to discharge liquid from above the inclined part (311) toward the inclined part (311) on the side opposite the particles (500) fixed to the inner surface of the container (12) across the central axis of the container (12).

The control unit (405) controls the nozzle (32) so as to suction the liquid in the container (12) until the particles (500) fixed on the inner surface of the container (12) are exposed from the liquid surface, and then discharge the liquid. After the discharge, the control unit (405) preferably controls the nozzle (32) so as to suction the liquid in the container (12), and thereafter discharge the liquid at a second discharge position different from the discharge position of the prior discharge on the inclined part (311) on the side opposite the particles (500) fixed to the inner surface of the container (12) with the central axis (300) of the container (12) interposed therebetween.

The object of the invention is a nucleic acid analyzer. In the embodiment, the nucleic acid analyzer includes the particle dispersing device, and a detection part (240) to amplify the nucleic acid in the liquid prepared by dispersing the particles (500) fixed to the inner surface of the container (12) by the particle dispersion device, and detecting the amplified nucleic acid.

According to the present invention, a strong shearing stress can be stably provided to the particles fixed to the inner surface of the container to disperse the particles efficiently.

BRIEF DESCRIPTION OF THE DRAWINGS

FIGS. 17A through 17D are vector diagrams of discharge fluid;
FIGS. 18A through 18D are vector diagrams of discharge fluid;
FIGS. 20A and 20B are shear stress distribution charts.

FIGS. 27A through 27D are shear stress distribution charts and shear stress maximum value transition charts;

FIGS. 29A through 29C show conventional particle suspension methods.

DETAILED DESCRIPTION OF THE PREFERRED EMBODIMENTS

1. Nucleic Acid Analyzer

In the embodiment, the particle dispersion is performed as a pretreatment in the analysis by a nucleic acid analyzer 100. That is, the nucleic acid analyzer 100 includes a function as a particle dispersion device and executes a particle dispersion method. In the embodiment, the particle dispersion device is a part of the nucleic acid analyzer 100, and has, for example, a setting part 110, a nozzle 32, and a control unit 405 described later. Note that particle dispersion also may be performed in an apparatus other than the nucleic acid analyzer 100, for example, an immunoassay device. An immunoassay device is a device for measuring blood or urine by immunoassay. The immunoassay is a measurement method utilizing an antigen-antibody reaction.

Figure 1:
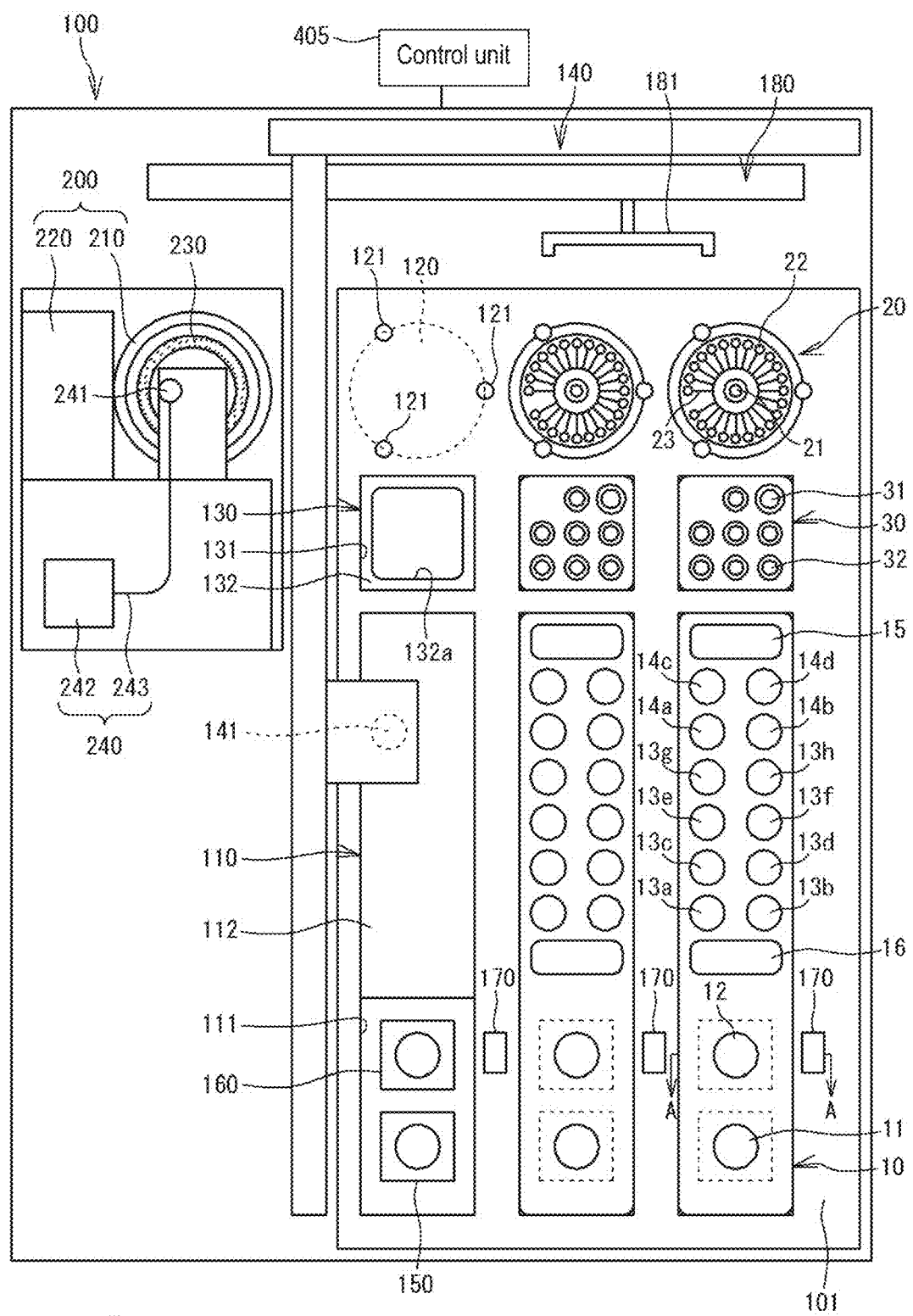
FIG. 1 is a schematic view of a nucleic acid analyzer as viewed from above.

In FIG. 1 showing the nucleic acid analyzer 100, the XYZ-axes are orthogonal to each other. In FIG. 1, the X-axis indicates the left and right direction, the Y-axis indicates the front and rear, and the Z direction indicates the vertical directions. Hereinafter, the positive direction of the Y-axis is the rear side of the device 100, and the negative direction of the Z-axis is the vertically downward direction. Also in the drawings below, the XYZ-axes are the same as the XYZ-axes shown in FIG. 1.

As shown in FIG. 1, the nucleic acid analyzer 100 includes a plate member 101. The plate member 101 is parallel to the XY-plane. Three first container setting parts 110, three second container setting parts 130, and three third container setting parts 130 are provided on the plate member 101.

The first container setting part 110 is an installation section for installing the first container 10. The first container setting part 110 is configured by an opening 111 formed in the plate member 101 and a support plate 112 located vertically below the plate member 101. In plan view, the opening 111 has a contour slightly larger than the outer shape of the first container 10, and the support plate 112 is provided on the rear side of the opening 111. The first container 10 is installed on the first container setting part 110 by supporting the lower end part 10b of the first container 10 in a vertically upward direction via the support plate 112 shown in FIG. 2A, and supporting the side surface of the first container 10 via the opening 111. When the analysis of the nucleic acid is started, the first container 10 is installed in the first container setting part 110.

Figure 2A:
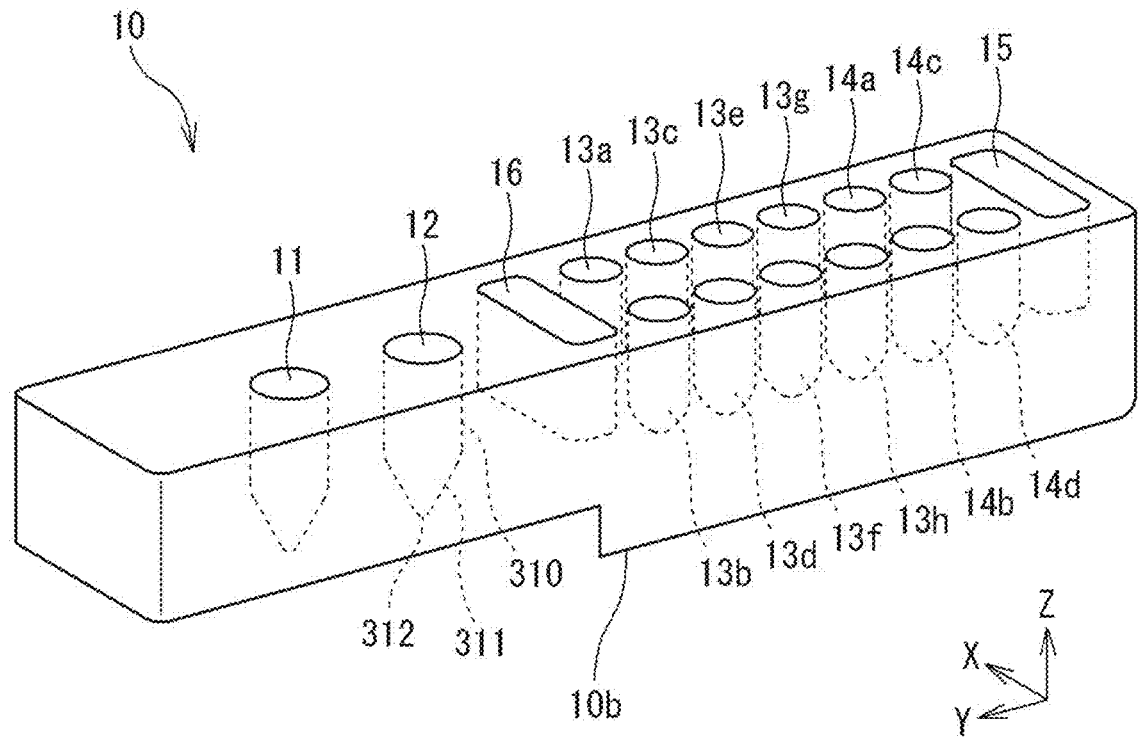
FIG. 2A is a perspective view of a first container.

As shown in FIG. 1 and FIG. 2A, the first container 10 includes a first reaction tank 11, a second reaction tank 12, reagent storage tanks 13a to 13h, mixing tanks 14a to 14d, a reagent storage part 15, and a waste liquid storage part 16. For example, an organic solvent is contained in the reagent container 15. The organic solvent is, for example, ethanol. The first reaction tank 11, the second reaction tank 12, the reagent storage tanks 13a to 13h, the mixing tanks 14a to 14d, the reagent storage part 15, and the waste liquid storage part 16 are provided in the first container 10, and are wells capable of containing a liquid. The second reaction tank 12 and tanks 13a to 13h already contain a reagent for nucleic acid extraction. The second reaction tank 12, the reagent storage tanks 13a to 13h, and the upper part of the waste liquid storage part 16 are sealed with an aluminum seal 10a. The reagent is contained in the reagent containing part 15 when the first container 10 is installed in the first container setting part 110.

The second reaction tank 12 already contains a reagent containing magnetic particles and a magnetic particle preservation solution. Magnetic particles are used to affix nucleic acids. Magnetic particles have a surface covered with silica with magnetic attribute. Silica has high hydrophobicity. Therefore, the magnetic particles covered with silica are hydrophobic. The particles constituting the magnetic particles are, for example, iron oxide. The magnetic particle preservation solution is, for example, sodium azide. Although magnetic particles are used for affixing the nucleic acid in the present embodiment, the invention is not limited thereto, and another measurement object such as an antigen or an antibody may be affixed.

The second reaction tank 12 is a tank in which adhered particles are agitated. The second reaction tank 12 has an inclined part 311 provided on the bottom side of a cylindrical body part 310. In the embodiment, the main body 301 has a cylindrical shape having a constant diameter viewed in the longitudinal direction. The upper part of the main body part 301 is open. In the embodiment, the inclined part 311 has a fixed angle of inclination, and the inner diameter linearly decreases from the main body part 310 side toward the bottom part side. The inner diameter is the inner diameter of the container 12. The inner diameter is the diameter of the inner surface of the container in the cross section orthogonal to the central axis 300 oriented in the longitudinal direction of the container. In the embodiment, the inclined part 311 is tapered to become narrower toward the bottom side. In this case, the taper 311 is a straight taper. In the second reaction tank 12, the tapered tip 312 has a rounded shape. As will be described later, the magnetic particles are fixed to the inner surface of the second reaction tank 12. Hereinafter, the second reaction tank 12 may be referred to as "container 12". Note that the first container setting part 110 is an installation section for installing the first container 10.

Each of the reagent storage tanks 13a to 13h respectively holds in advance a solubilizing solution, proteinase K, oil, eluate, stock solution of the extraction reagent, stock solution of the second washing solution, stock solution of the dilution liquid, and stock solution of the first washing solution.

As shown in FIG. 1, the second container setting part 120 is a setting part for installing the second container 20. The second container setting part 120 is configured by an upper surface of the plate member 101, and three pins 121 installed on the upper surface of the plate member 101. The second container 20 is installed in the second container setting part 120 by engaging an engage part 27a of the second container 20 described later with the three pins 121.

The second container 20 includes an injection port 21, twenty-three amplification parts 22, and twenty-three flow paths 23 connecting the injection port 21 and the twenty-three amplification parts 22. The second container 20 is a disk-shaped container in which the injection port 21 is arranged at the center position, and the twenty-three amplification parts 22 are arranged at regular intervals in the circumferential direction at positions on the outer peripheral side of a constant diameter from the center position. The center position of the second container 20 is the rotational center when the second container 20 is rotated as described later.

Figure 2B:
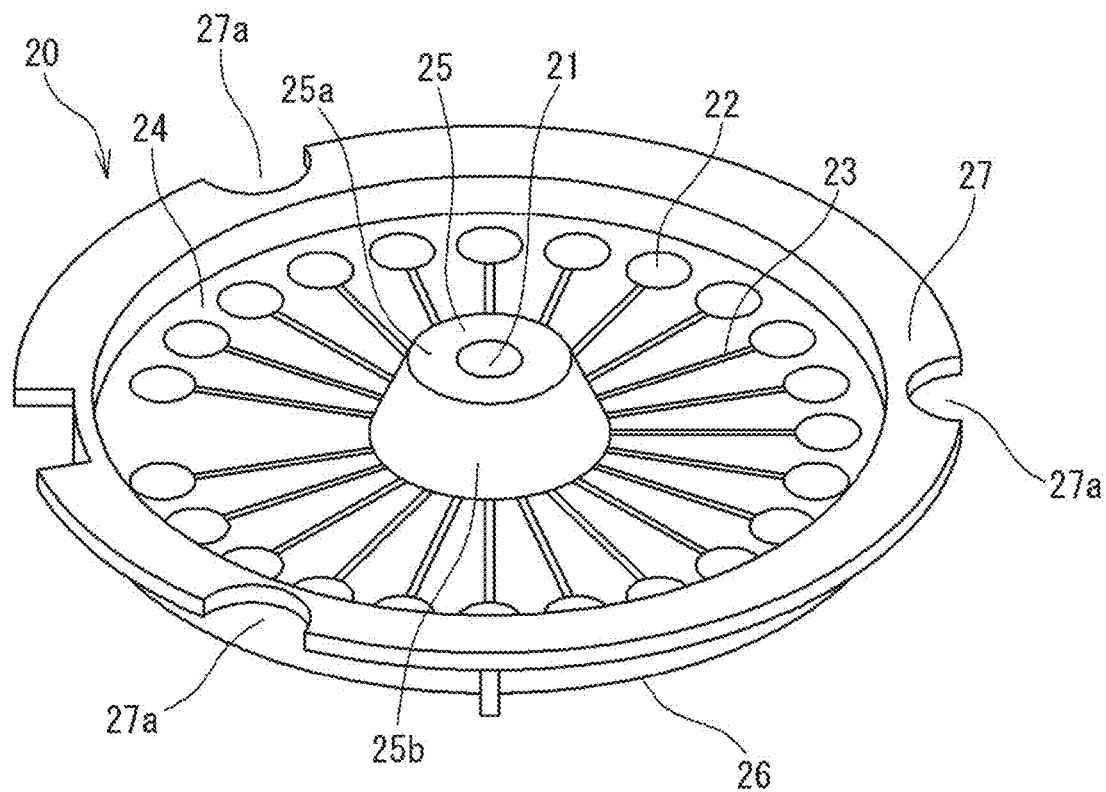
FIG. 2B is a perspective view of a second container.

Specifically, as shown in FIG. 2B, the second container 20 includes an upper surface part 24, a projection 25, a lower surface part 26, and a flange part 27. The protrusion 25 is arranged at the center position of the second container 20. The protrusion 25 is axially symmetric about the straight line parallel to the vertical direction passing through the central axis of the second container 20 with the thickness in the vertical direction narrowed toward the end part of the second container 20. The protrusion 25 includes an upper surface part 25a and an inclined surface part 25b. The upper surface of the upper surface part 25a is parallel to the horizontal surface. The injection port 21 is formed in the upper surface part 25a and is a hole parallel to the vertical direction.

The upper surface part 24 is made of a light-transmitting member. The upper surface of the upper surface part 24 is parallel to the horizontal surface, and recessed parts and grooves for respectively forming the amplification part 22 and the flow path 23 are formed on the lower surface of the upper surface part 24. The amplification part 22 and the flow path 23 are formed by attaching the thin film-like ABS resin to the lower surface of the upper surface part 24. The lower surface part 26 is made of thin-film aluminum having high thermal conductivity. The lower surface part 26 is affixed to the ABS resin adhered to the lower surface of the upper surface part 24 from the lower side.

The flange part 27 is a flat plate parallel to the horizontal plane formed outside the upper surface part 24. Three engage parts 27a are formed on the flange part 27. The engage part 27a is a notch. The engage part 27a engages the engaging part 214 of the container setting part 210 described later. The engage portion 27a may be engaged with the engaging part 214 of the container setting part 210, and instead of a notch, a hole, a recess, a protrusion, or the like may be used.

An extraction liquid containing nucleic acid extracted in the first container 10 positioned on the X-axis positive side is injected into the injection port 21. The amplification part 22 already contains a reagent for amplifying the nucleic acid in the extraction liquid. The second container 20 is a reaction container for reacting the extract liquid injected from the injection port 21 with the reagent of the amplification part 22.

As shown in FIG. 1, the third container setting part 130 is a setting part for installing the third container 30. The third container setting part 130 is configured by an opening 131 formed in the plate member 101, and a support plate 132 located vertically below the plate member 101. In plan view, the opening 131 has a slightly larger contour than the contour of the second container 30. An opening 132a is formed in the support plate 132. In the third container 30 is installed on the third container setting part 130 by passing the body part of the third container 30 through the opening 132a, and supporting the lower surface 30a of the flange part formed on the outer periphery of the third container 30 shown in FIG. 3A vertically above by the support plate 132. When the analysis of the nucleic acid starts, the first container 10 is installed in the first container setting part 110.

As shown in FIGS. 1 and 3A, the third container 30 holds one piercing tip 31 and seven pipette tips 32. The piercing tip 31 is for puncturing the aluminum seal of the first container 10 to open the upper part of the accommodating portion on the lower side of the aluminum seal. The pipette tip 32 has a hole penetrating in the vertical direction. As shown in FIGS. 3A and 3B, when the suction part 141 of the dispensing unit 140 is lowered from directly above the pipette tip 32, the pipette tip 32 is attached to the lower end of the suction part 141. Then, as the suction part 141 moves upward, the pipette tip 32 is pulled out from the second container 30. Similarly, the piercing tip 31 is attached to the lower end of the suction part 141. In the suction part 141, a hole 141a is formed so that liquid can be suctioned and discharged from the lower end of the suction part 141. In the embodiment, the pipette tip 32 attached to the suction part 141 functions as a nozzle for discharging and suctioning the reagent. Hereinafter, the pipette tip 32 may be referred to as "nozzle 32". Note that the pipette tip 32 also need not be attached to the suction part 141 and the suction part 141 may function as a nozzle.

In the nucleic acid analyzer 10 according to the embodiment, disposable pipette tips 32 are attached to the lower end of the suction part 141 to prevent contamination. In the nucleic acid analyzer 10 according to the embodiment, suctioning and discharging of liquid are performed from the lower end of the pipette tip 32 attached to the lower end of the suction part 141.

As shown in FIG. 1, the nucleic acid analyzer includes a dispensing unit 140. The dispensing unit 140 transfers the extract liquid stored in the first container 10 from the first container 10 to the injection port 21 of the second container 20. As shown in FIG. 3C, the dispensing unit 140 includes a suction part 141, a drive part 142, and transfer parts 143, 144, and 145. The suction part 141 is detachable from the piercing tip 31 and the pipette tip 32. The suction part 141 is configured by the nozzle. The drive part 142 is configured by, for example, a pump 142. The pump 142 is connected to the hole 141a of the suction part 141. The pump 142 applies a positive pressure and a negative pressure to the suction part 141 and suctions and discharges the liquid via the pipette tip 32 attached to the lower end of the suction part 141.

The transfer parts 143, 144, and 145 include a vertical transfer part 143. The vertical transfer part 143 includes a rail 143a extending along the Z-axis, and a step motor (not shown). The vertical transfer part 143 drives the step motor to transfer the suction part 141 in the Z-axis direction along the rail 143a. The transfer parts 143, 144, and 145 include a front-rear transfer part 144. The front-rear transfer part 144 includes a rail 144a extending along the Y-axis, and a step motor (not shown). The rail 144a is a rail for moving the suction part 141 along the Y-axis. The front-rear transfer unit 144 drives the step motor to transfer the vertical transfer unit 143 in the Y-axis direction along the rail 144a. The transfer parts include a left-right transfer part 145. The left-right transfer part 145 includes a rail 145a extending along the X-axis, and a step motor (not shown). The rail 145a is a rail for moving the suction part 141 along the X-axis. The left-right transfer part 145 drives the step motor to transfer the front-rear transfer part 144 in the X-axis direction along the rail 145a.

The suction part 141 can move along the XYZ-axes inside the nucleic acid analyzer 100 by the transfer parts 143, 144, 145. The dispensing unit 140 transfers the extract liquid from the first container 10 to the second container 20 along the Y-axis. More specifically, the dispensing unit 140 suctions the extract liquid from the first container 10 with the pipette tip 32 attached to the suction part 141. Thereafter, the dispensing unit 140 moves the pipette tip 32 to the injection port 21 of the second container 20 disposed on the negative Y-axis side of the first container 10 from which the extract liquid was suctioned. Then, the dispensing unit 140 discharges the extract liquid to the second container 20 from the injection port 21.

In addition, the dispensing unit 140 moves to the second reaction tank 12 and disperses the magnetic particles in the second reaction tank 12 by discharging the reagent into the second reaction tank 12.

Figure 4:
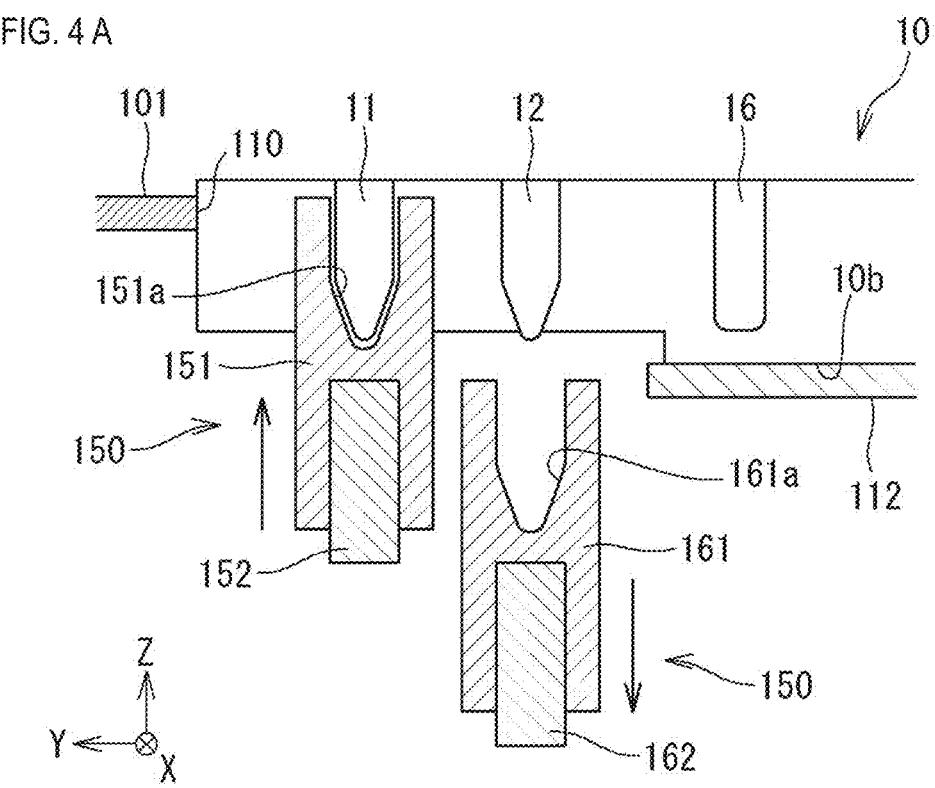
FIG. 4A is a cross-sectional view of a temperature control unit.
FIG. 4B is a layout view of magnets.
Figure 4:
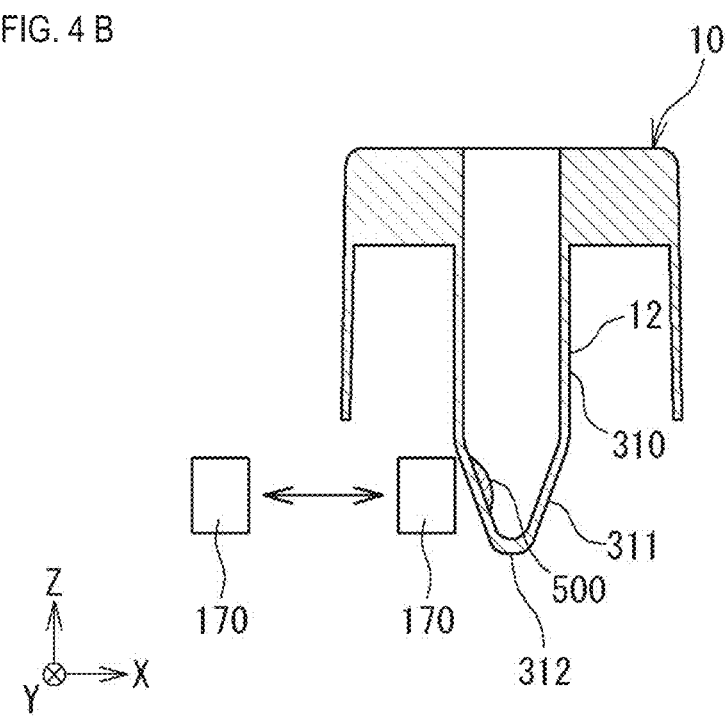

As shown in FIG. 1, the nucleic acid analyzer 100 includes temperature adjustment parts 150 and 160. The temperature control parts 150 and 160 are disposed in front of the opening 111 of the first container setting part 110 in plan view. As shown in FIG. 4A, the temperature control part 150 includes a heat block 151 and a heater 152, and heats the first reaction tank 11 of the first container 10 installed in the first container setting part 110. A hole 151a having substantially the same shape as the shape of the first reaction tank 11 is formed in the heat block 151. When the first reaction tank 11 is heated, the temperature control part 150 is moved upward and the first reaction tank 11 is accommodated in the hole 151a. In this state, the heat of the heater 152 is transmitted to the first reaction tank 11 via the heat block 151. When heating of the first reaction tank 11 is completed, the temperature control part 150 is moved downward.

Similarly, the temperature control part 160 includes a heat block 161 and a heater 162, and heats the second reaction tank 11 of the first container 10 installed in the first container setting part 110. When the second reaction tank 11 is heated, the temperature control part 160 is moved upward and the second reaction tank 11 is accommodated in the hole 161a. In this state, the heat of the heater 162 is transmitted to the second reaction tank 12 via the heat block 161. When heating of the second reaction tank 12 is completed, the temperature control part 160 is moved downward.

As shown in FIG. 1, the nucleic acid analyzer 100 includes a magnet 170 for laying the magnetic particles 500 on the inner surface of the first container 10. The magnet 170 is disposed vertically below the plate member 101 and is provided close to and away from the second reaction tank 12 of the first container 10 installed in the first container setting unit 110. When the magnet 170 approaches the second reaction tank 12, as shown in FIG. 4A, the temperature control unit 160 retreats vertically downward. As the magnet 170 approaches the second reaction tank 12, the magnetic particles 500 contained in the second reaction tank 12 are attracted to the magnet 170 as shown in FIG. 4B, and the magnetic particles 500 aggregate and are fixed to the contained in the second reaction tank 12 on the wall surface on the X-axis negative side of the second reaction tank 12. In the embodiment, the magnetic particles 500 aggregate only on one side (negative side) in the X-axis direction and do not aggregate on the other side (positive side). That is, the magnetic particles 500 are not entirely fixed in the circumferential direction of the second reaction vessel 12 but rather are locally fixed in the circumferential direction.

As shown in FIG. 1, the nucleic acid analyzer 100 includes a transfer unit 180. The transfer unit 180 includes a hand part 181 and a mechanism for moving the hand part 181 along the X-axis direction. The transfer unit 180 grips and transfers the second container 20 between the second container setting part 120 and the position of the rotating part 200. The transfer unit 180 transfers the second container 20 installed in the second container setting part 120 to the position of the rotating part 200 by injecting the extract liquid. Instead of gripping and transferring the second container 20 by the hand part 181, the transfer unit 180 may suction and transfer the upper surface of the upper surface part 24 of the second container 20 by the suction part.

As shown in FIG. 1, the nucleic acid analyzer 100 includes a rotating part 200. The rotating part 200 includes a container setting part 210 and a rotation drive part 220. A second container 20 is installed in the container setting part 210. The rotating part 200 rotates the second container 20 injected with the extract liquid so as to send the extract liquid to the amplification part 22 by centrifugal force via the flow path 23. Specifically, the rotation drive part 220 rotates the container setting section 210 where the second container 20 is installed by applying a drive force to the first outer surface 212 of the container setting part 210, which will be described later, so that the second container 20 is rotated by the rotation of the container setting part 210 to send the extract liquid injected from the injection port 21 to the amplification part 22 by centrifugal force via the flow path 23. The first temperature control part 230 is rotated by the rotating part 200 so as to generate a nucleic acid amplification reaction in the amplification part 22, and adjusts the temperature of the second container 20 installed in the container setting part 210. The first temperature control part 230 is configured by a Peltier element.

At this time, in the amplification part 22, the nucleic acid contained in the extract liquid is mixed with the reagent previously stored in the amplification part 22 to prepare a mixed solution of the nucleic acid and the reagent. The amplification unit 22 stores in advance a reagent that amplifies the detection target nucleic acid in which a mutation occurs in a detection target part of the nucleic acid, and a reagent that includes a fluorescent probe that binds to the detection target nucleic acid. The fluorescent probe contains a fluorescent substance. When the fluorescent probe binds to the detection target nucleic acid, the detection target nucleic acid is labeled with the fluorescent substance. When the fluorescent probe is bound to the detection target nucleic acid and excitation light is irradiated to the fluorescent substance of the fluorescent probe, fluorescence is generated from the fluorescent substance. Alternatively, when the fluorescent probe is not bound to the detection target nucleic acid and excitation light is irradiated to the fluorescent substance of the fluorescent probe, fluorescence is not generated from the fluorescent substance.

A nucleic acid amplification reaction occurs in the amplification part 22 when the temperature is regulated by the first temperature control part 230. The detection target nucleic acid is amplified in the amplification part 22 when the detection target nucleic acid is contained in the nucleic acid, and the amplification section 22 does not amplify the detection target nucleic acid when the detection target nucleic acid is not contained in the nucleic acid. Therefore, when the detection target nucleic acid is amplified, fluorescent light is generated according to the amount of amplification when excitation light is irradiated by the amplification part 22 since the amplified detection target nucleic acid is labeled with the fluorescent substance of the fluorescent probe.

The rotating part 200 moves the amplification parts 22 so that the temperature-adjusted amplification parts 22 are sequentially positioned at the detection position by the detecting part 240. More specifically, the rotation drive part 220 rotates the container setting part 210 to sequentially position the amplification parts 22 of the second container 20 installed in the container setting part 210 at the detection position in accordance with the determined order.

As shown in FIG. 1, the nucleic acid analyzer 100 includes a detection part 240. The detection part 240 detects a nucleic acid amplification reaction occurring in the amplification part 22 positioned at the detection position by the rotating part 200. Specifically, the detection part 240 detects the intensity of the fluorescence signal indicating the amount of the amplification product by the nucleic acid amplification reaction.

Figure 5:
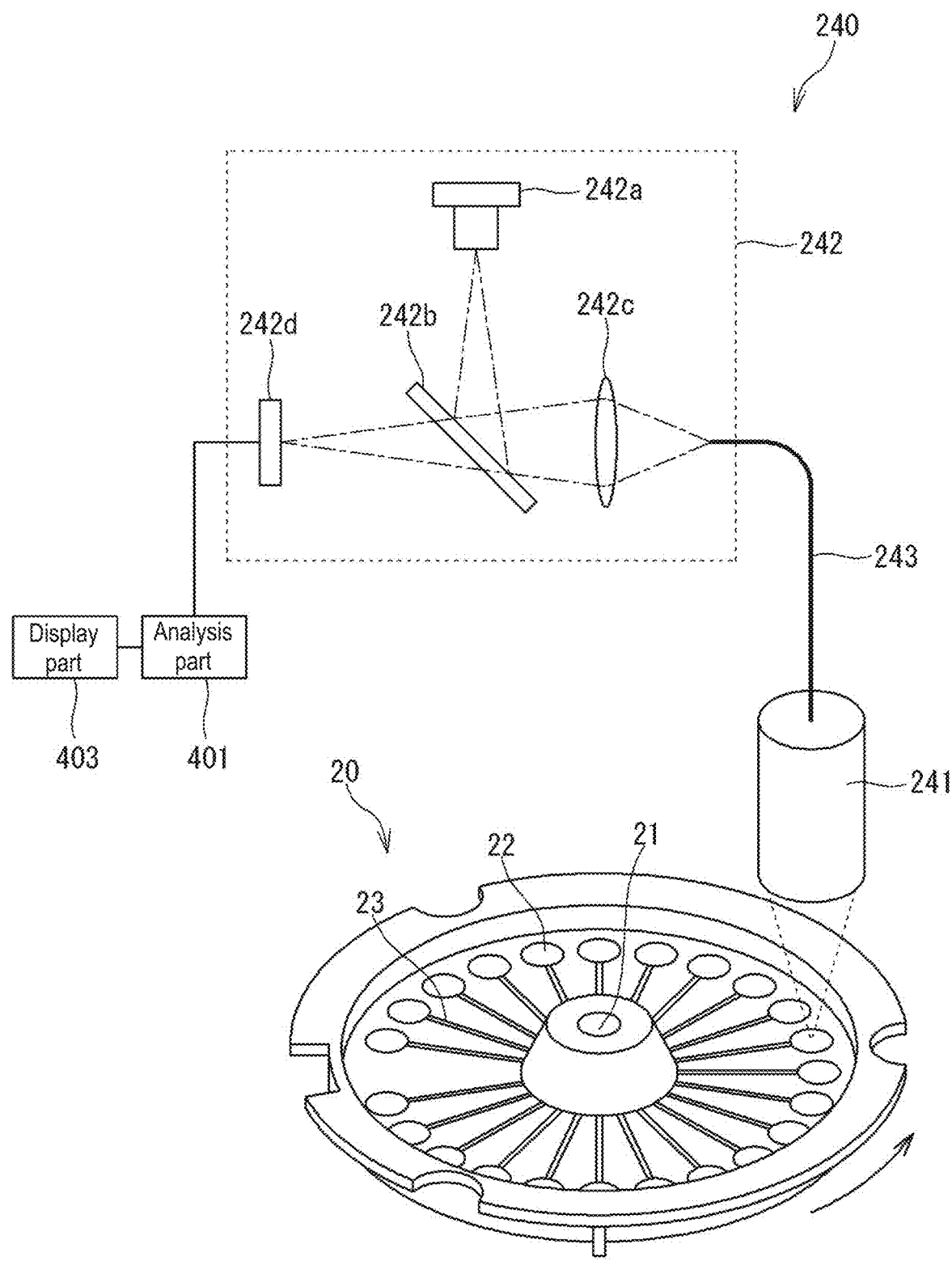
FIG. 5 is a structural view of the detection part.

As shown in FIG. 1 and FIG. 5, the detection part 240 includes a detection head 241 and an optical unit 242 connected to the detection head 241 via an optical fiber 243. The detection part 240 irradiates the amplification part 22 of the second container 20 with light to detect a nucleic acid amplification reaction. The detection head 241 is arranged to face the amplification part 22 of the second container 20 to irradiate the amplification part 22 with light. The optical unit 242 includes a light source 242a, a dichroic mirror 242b, a condenser lens 242c, and a photodetector 242d.

The light source 242a emits excitation light of a predetermined wavelength. The excitation light emitted from the light source 242a excites the fluorescent substance of the fluorescent probe to generate fluorescent light when the fluorescent probe is bound to the detection target substance. The dichroic mirror 242b reflects the excitation light emitted from the light source 242a and transmits fluorescent light generated from the fluorescent substance of the fluorescent probe. The condenser lens 242c collects the excitation light reflected by the dichroic mirror 242b and guides the light to the optical fiber 243. The condenser lens 242c also collects the fluorescent light emitted from the optical fiber 243 to the condenser lens 242c and guides the light to the dichroic mirror 242b. The photodetector 242d receives the fluorescent light transmitted through the dichroic mirror 242b, measures the intensity of the received fluorescent light, and outputs an electric signal corresponding to the intensity of fluorescent light.

As shown in FIG. 5, the nucleic acid analyzer 100 includes an analyzing part 401. The analyzing part 401 generates a plurality of time series data indicating the nucleic acid amplification reaction occurring in each amplification part 22 from the fluorescence electric signal detected by the photodetector 242d of the detection part 240. Then, based on the time-series data, the analyzing part 401 determines whether the detection target substance is included in each amplification part 22, and displays the determination result or the like on a display part 403. Analysis of the nucleic acid is completed in this way.

As shown in FIG. 1, the nucleic acid analyzer 100 includes control unit 405. The control unit 405 may be configured by a CPU or a microcomputer. The control unit 405 controls the operation for particle dispersion and other operations of the nucleic acid analyzer 100.

Figure 6:
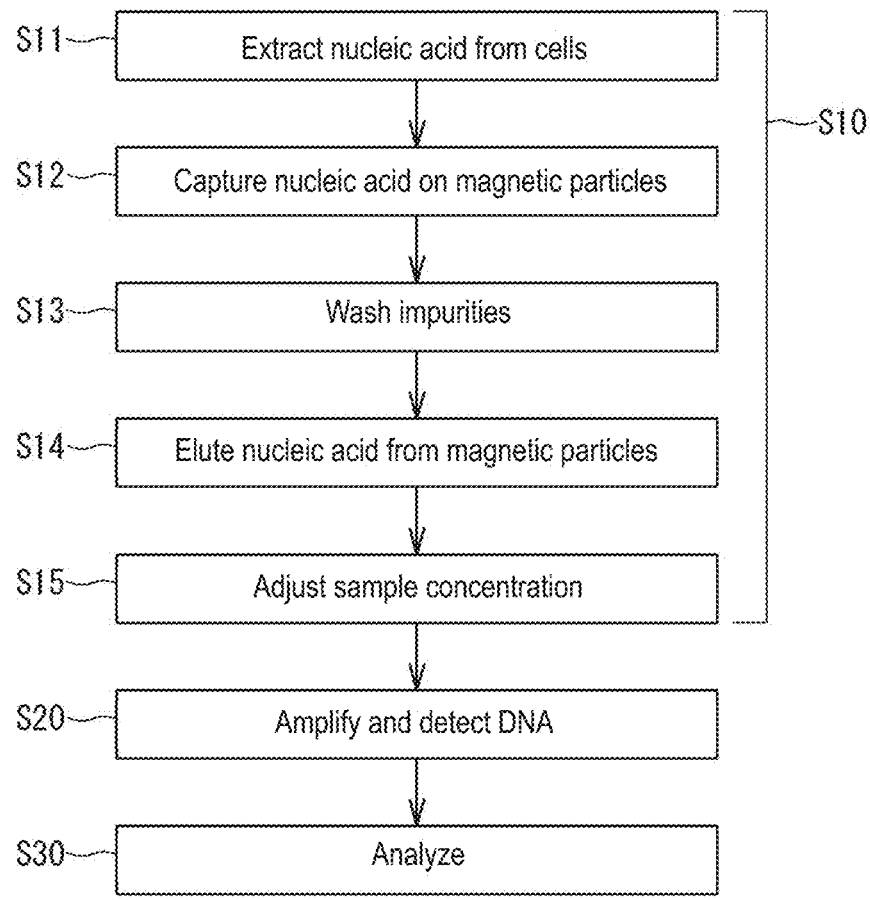
FIG. 6 is a process chart of capturing nucleic acid on magnetic particles.

FIG. 6 shows a processing procedure of the nucleic acid analyzer 100. The nucleic acid analyzer 100 extracts and purifies the nucleic acid in step S10, amplifies and detects the nucleic acid in step S20, and analyzes in step S30.

The nucleic acid extraction-purification step of step S10 is controlled by a control unit 40 and includes steps S11 to S15 shown in FIG. 6. In step S11, nucleic acids are extracted from the cells. The nucleic acid is extracted in the first reaction tank 11. The nucleic acid extracted in step S12 is captured by the magnetic particles. The nucleic acid is captured in the second reaction tank 12. The impurities contained in the captured nucleic acid are washed (B/F separation) in step S13. In step S14, the nucleic acid is eluted from the magnetic particles. Impurity washing and nucleic acid elution are also performed in the second reaction tank 12. In step S14, the concentration of the sample containing the nucleic acid eluted from the magnetic particles is adjusted.

Figure 7:
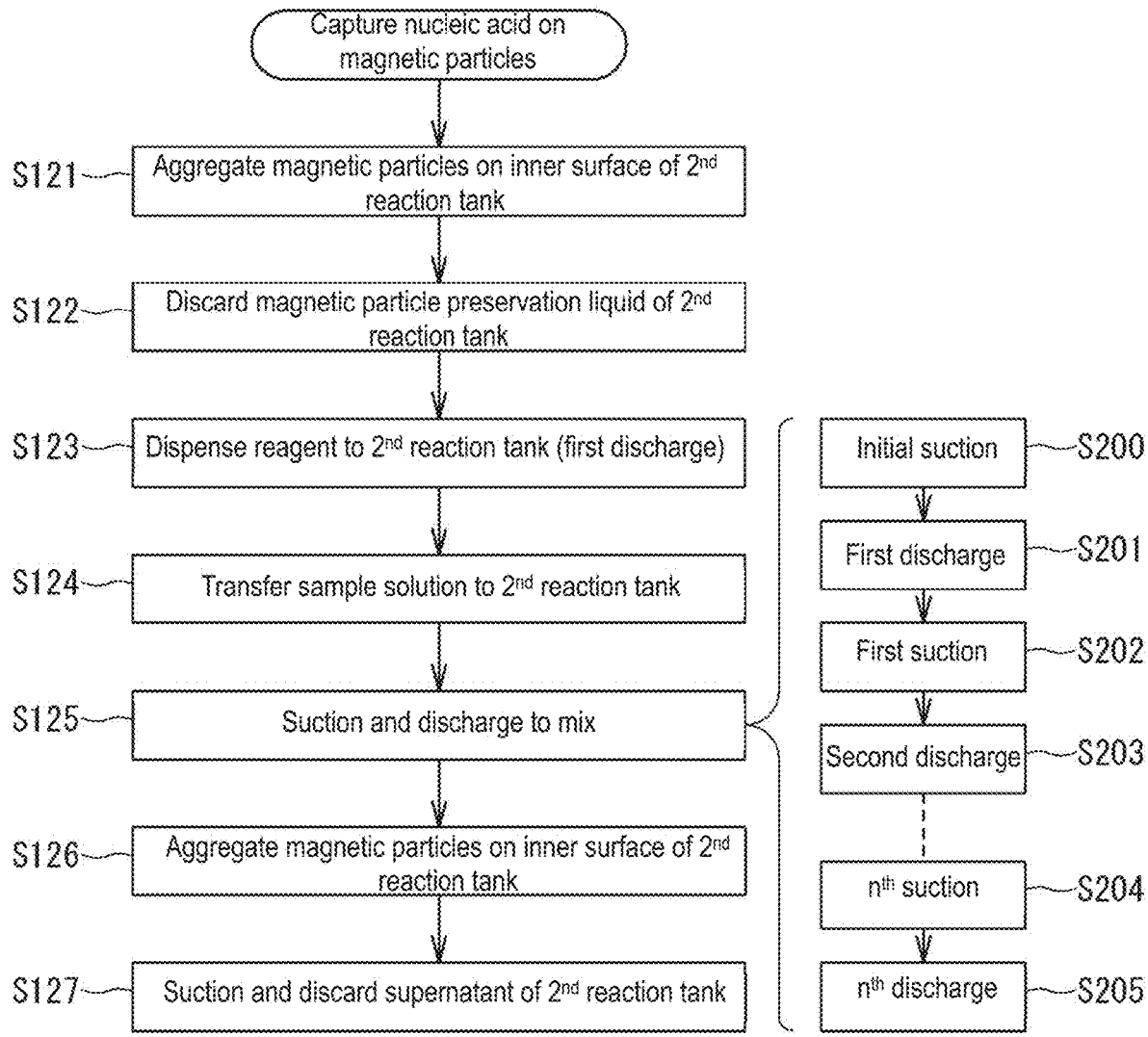
FIG. 7 is a process chart of cleaning impurities.

FIG. 7 shows details of step S12 of capturing nucleic acid on magnetic particles. In step S121, the control unit 405 brings the magnet 170 close to the second reaction tank 12. As the magnet 170 approaches the second reaction tank 12 (see FIG. 4B), the magnetic particles 500 adhere to the inner surface of the second reaction tank 12. Note that, as described above, the second reaction vessel 12 already contains a reagent that includes magnetic particles and a magnetic particle preservation solution.

Subsequently, in step S122, the control unit 405 causes the dispensing unit 140 to suction the magnetic particle preservation solution in the second reaction tank 12 and discard it. Note that, when the discarding is completed, the control unit 405 separates the magnet 170 from the second reaction tank 12.

In step S123, the control unit 405 causes the dispensing unit 140 to dispense a mixture of the extraction reagent and ethanol in the reagent storage part 15 into the second reaction tank 12. By dispensing a mixed solution of the extraction reagent and ethanol, the magnetic particles 500 fixed to the second reaction tank 12 are immersed in the mixed solution.

In step S124, the control unit 405 moves the sample solution containing the extracted nucleic acid from the first reaction tank 11 to the second reaction tank 12 by the dispensing unit 140.

In step S125, the magnetic particles 500 fixed to the inner surface of the second reaction tank 12 are dispersed in the liquid of the second reaction tank 12. In order to disperse the magnetic particles, the control unit 405 causes the dispensing unit 140 to suction and discharge the liquid in the second reaction tank 12. By discharging the liquid to the second reaction tank 12, the fixed magnetic particles are peeled off and dispersed in the liquid. The magnetic particles can attach the nucleic acid to the amplification part 22 by the dispersion of the magnetic particles in the second reaction tank 12. Note that suction and discharge are performed a plurality of times, and this aspect will be described later.

In step S126, the control unit 405 brings the magnet 170 close to the second reaction tank 12. When the magnet 170 approaches the magnet 170 in the second reaction tank 12, the magnetic particles 500 bearing the captured nucleic acid are fixed to the inner surface of the second reaction tank 12.

In step S127, the control unit 405 causes the dispensing unit 140 to suction the supernatant of the second reaction tank 12 and discard it. When the discarding is completed, the control unit 405 separates the magnet 170 from the second reaction tank 12.

Figure 8:
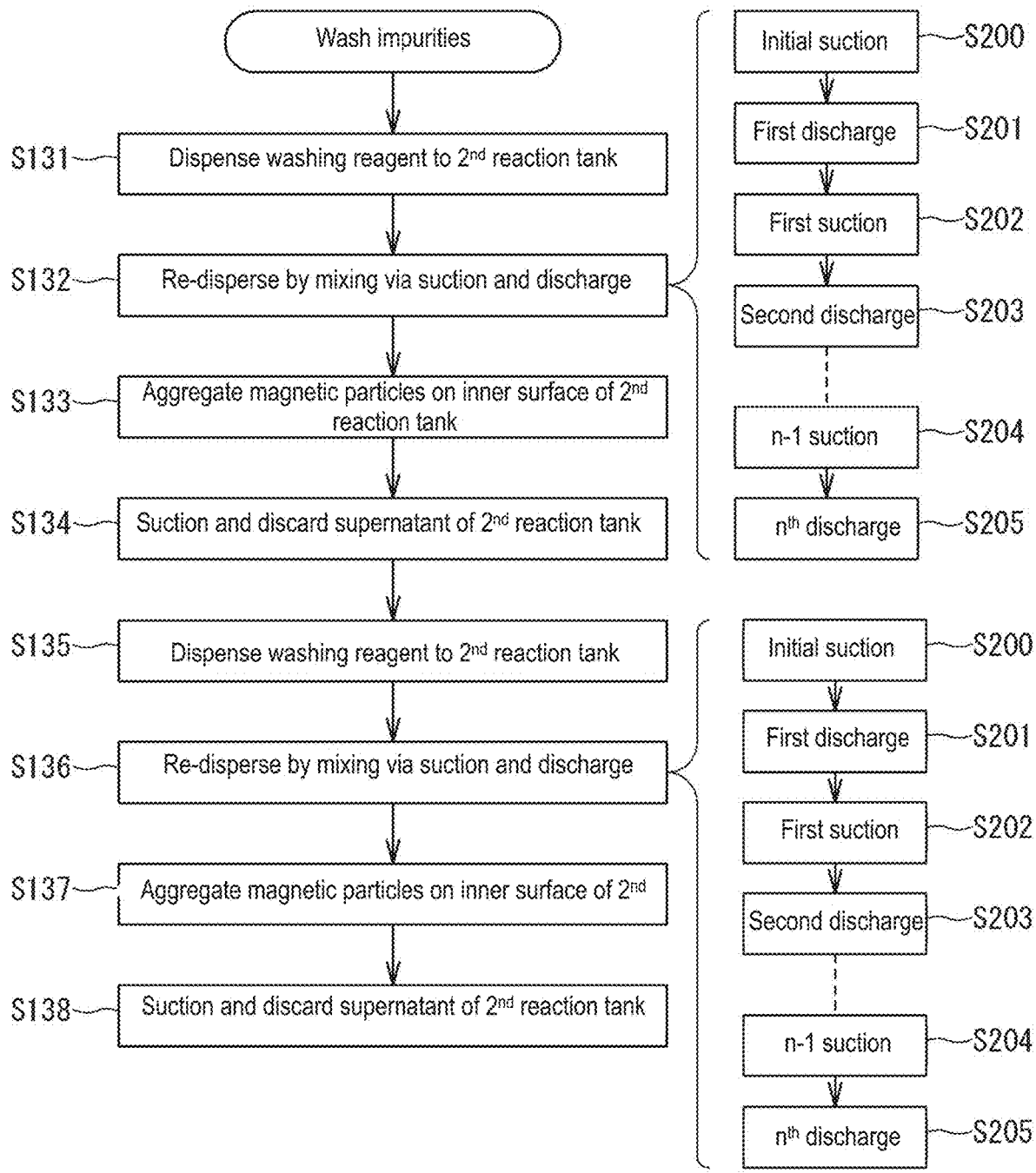
FIG. 8 is a process chart of eluting nucleic acid from magnetic particles.

FIG. 8 shows details of step S13 for washing impurities. In step S131, the control unit 405 causes the dispensing unit 140 to dispense a mixture of the washing reagent and ethanol into the second reaction tank 12. By dispensing a mixed solution of the washing reagent and ethanol, the magnetic particles 500 fixed to the second reaction tank 12 are immersed in the mixed solution.

In step S132, the magnetic particles 500 fixed to the inner surface of the second reaction tank 12 are dispersed in the mixed liquid of the second reaction tank 12. In order to disperse the magnetic particles, the control unit 405 causes the dispensing unit 140 to suction and discharge the mixed liquid in the second reaction tank 12. By discharging the liquid to the second reaction tank 12, the fixed magnetic particles are peeled off and dispersed in the liquid. Note that, also in step S132, suction and discharge are performed a plurality of times, which will be described later.

In step S133, the control unit 405 brings the magnet 170 close to the second reaction tank 12. When the magnet 170 approaches the magnet 170 in the second reaction tank 12, the magnetic particles 500 adhere to the inner surface of the second reaction tank 12.

In step S134, the control unit 405 causes the dispensing unit 140 to suction and discard the supernatant of the second reaction tank 12. When the discarding is completed, the control unit 405 separates the magnet 170 from the second reaction tank 12.

In steps S131 to 134, the first washing is completed. Subsequently, in steps S135 to S138, the second washing is performed. Since the second washing step is the same as the first washing step, a description will be omitted.

Figure 9:
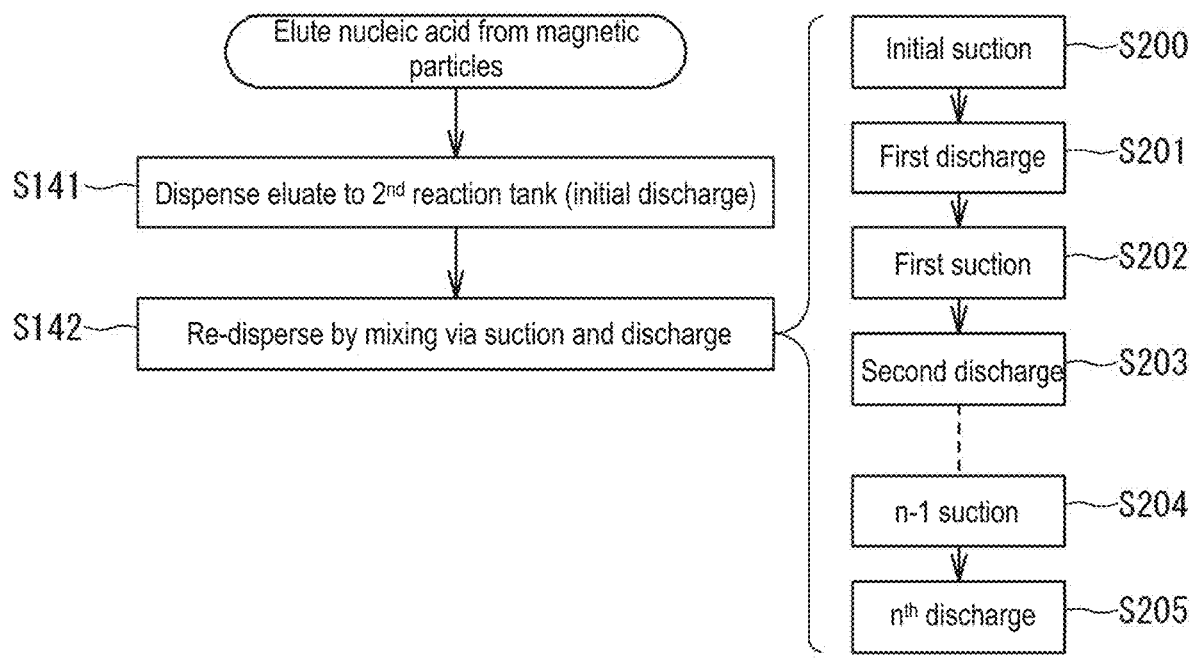
FIG. 9 is an illustration of a discharge position and a suction position.

FIG. 9 shows details of step 14 of eluting nucleic acids from magnetic particles. In step S141, the control unit 405 causes the dispensing unit 140 to dispense the eluate into the second reaction tank 12. By dispensing the eluate, the magnetic particles 500 fixed to the second reaction tank 12 are immersed in the eluate.

In step S142, the magnetic particles 500 fixed to the inner surface of the second reaction tank 12 are dispersed in the eluate of the second reaction tank 12. In order to disperse the magnetic particles, the control unit 405 causes the dispensing unit 140 to suction and discharge the eluate in the second reaction tank 12. By discharging the eluate to the second reaction tank 12, the fixed magnetic particles are peeled off and dispersed in the eluate. Note that, also in step S142, suction and discharge are performed a plurality of times, which will be described later.

2. Stirring by Suction and Discharge

As described above, the dispersion of the magnetic particles 500 by suction and discharge is performed in step S125 in FIG. 7, steps S132 and S136 in FIG. 8, and step S142 in FIG. 9. As shown from step S200 to step S205 in each of FIGS. 7, 8 and 9, suction and discharge are performed a plurality of times.

In the plurality of suction and discharge operations, the control unit 405 causes the drive unit 142 to perform initial suction in step S200 prior to the first discharge (first discharge: step S201). The initial suction is performed in order to expose the magnetic particles 500 immersed in the liquid from the liquid level. Since the reagent is dispensed as the initial discharge in the second reaction tank 12 in step S123, step S131 or step S141, the magnetic particles 500 are immersed in the reagent during the time before initial suction.

In order to apply a high shear stress to the magnetic particles 500 it is preferable to apply the discharge liquid to the magnetic particles 500 exposed to the atmosphere rather than to apply the discharge liquid to the magnetic particles 500 in the liquid in as much as high shear stress is easily obtained by a thin layer flow, and particularly when liquid strikes first with particles immediately after discharge.

Figure 10:
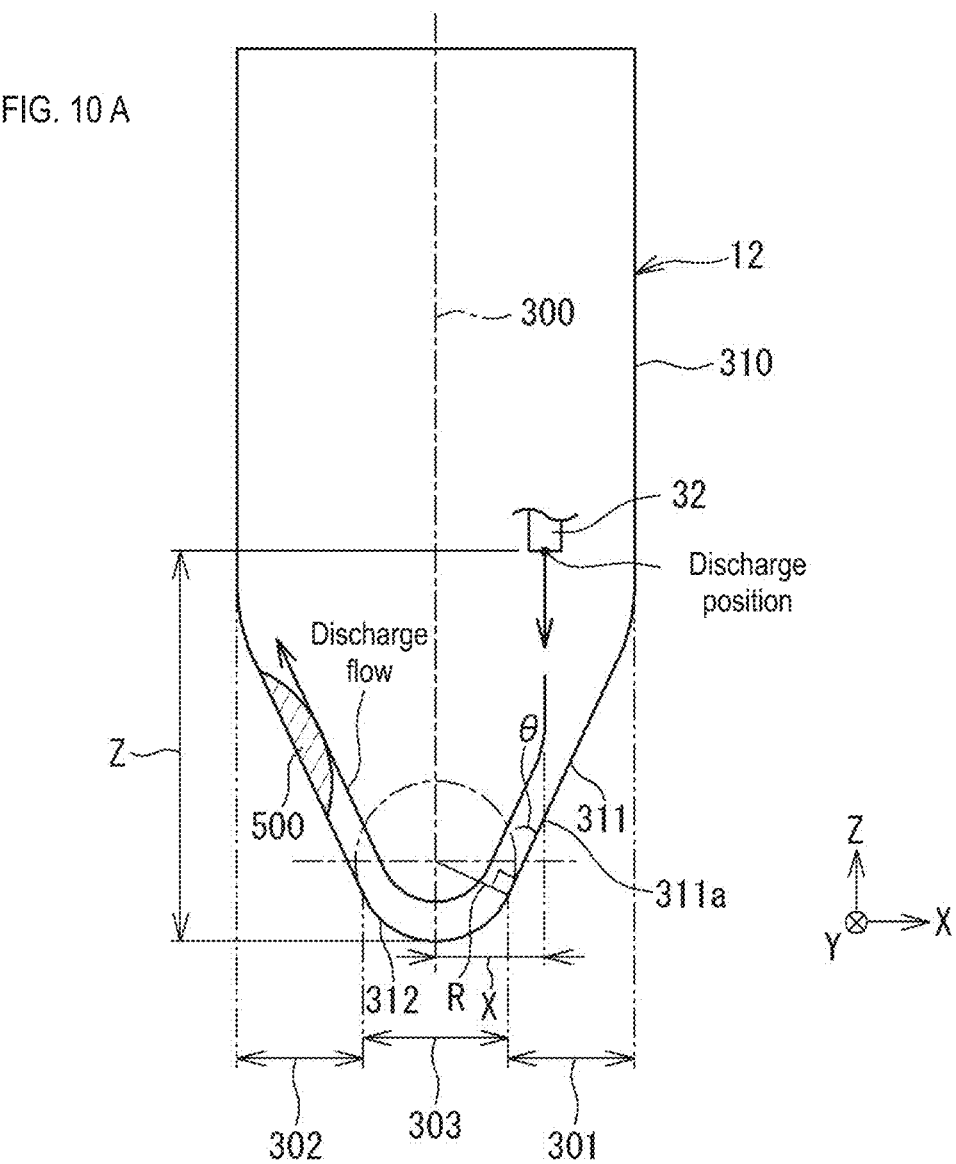
FIGS. 10A and 10B are illustrations of particle dispersion according to the embodiment.
Figure 10:
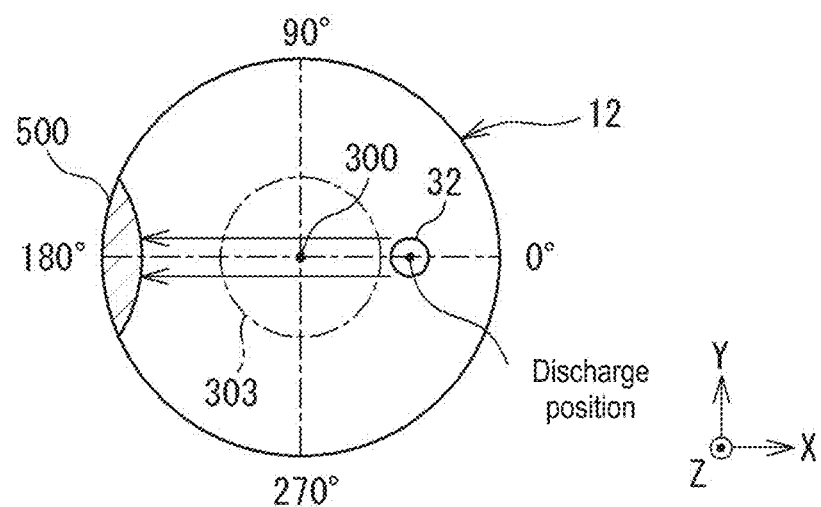

In the state in which the magnetic particles 500 are exposed to the atmosphere by the initial suction, the control unit 405 causes the drive part 142 to perform the first discharge in step S201 in order to detach the fixed magnetic particles 500. As shown in FIG. 10, the first discharge is directed to the opposite side (the positive side in the X-axis direction) of the particles 500 on the negative side in the X-axis direction across the central-axis 130 of the second reaction vessel 12, from the nozzle 32 (pipette tip 32) at the first ejection position included in the range 301 directly above the inclined part 311 toward the inclined part 311. The control unit 405 controls the transfer parts 143, 144, and 145 to transfer the nozzles 32 (pipette tips 32) to the first discharge position prior to the first discharge; note that the initial suction also can be omitted when a sample is added to the second reaction tank 12 by the first discharge in S201.

The nozzle 32 (pipette tip 32) positioned immediately above the inclined part 311 discharges the reagent downward from the tip thereof, causing the reagent to strike the inclined part 311 where the particles 500 are not fixed. Discharging is performed a plurality of times in order to surely separate the particles 500. The number of discharges n is, for example, several tens of times. Each discharge is performed at a discharge position included in the range 301 that is on the side opposite the particles 500 and on the opposite side of the central axis 130 of the container 12 and directly above the inclined part 311. In each of step S125, step S132, step S136, and step S142, the number of discharges n is not necessarily the same and may be different. The magnetic particles are very strongly fixed in step S125 prior to capture of nucleic acid and step S132 in first washing immediately after nucleic acid capture. That is, before the nucleic acid capture, the particles 500 tend to aggregate strongly since the magnetic particles 500 hydrophobic. Immediately after capturing the nucleic acid, the particles 500 also tend to aggregate strongly since there are a lot of impurities. Therefore, it is preferable to perform more discharges in step S125 prior to nucleic acid capture and step S132 in the first washing immediately after nucleic acid capture.

The control unit 405 causes the drive part 142 to suction the discharged liquid so as to expose the magnetic particles 500 from the liquid surface during each discharge. For example, the first suction in step S202 is performed between the first discharge in step S201 and the second discharge in step S203. As with the initial suction, these suctions are performed in order to expose the magnetic particles 500 to the atmosphere and obtain a high shear stress in the next discharge. The suction is also to expose the position 311a where the discharged liquid strikes first in the inclined part 311. The exposure at the position 311a is effective for generating a stable liquid flow at the initial stage of discharge and obtaining high shear stress.

Figure 11B:
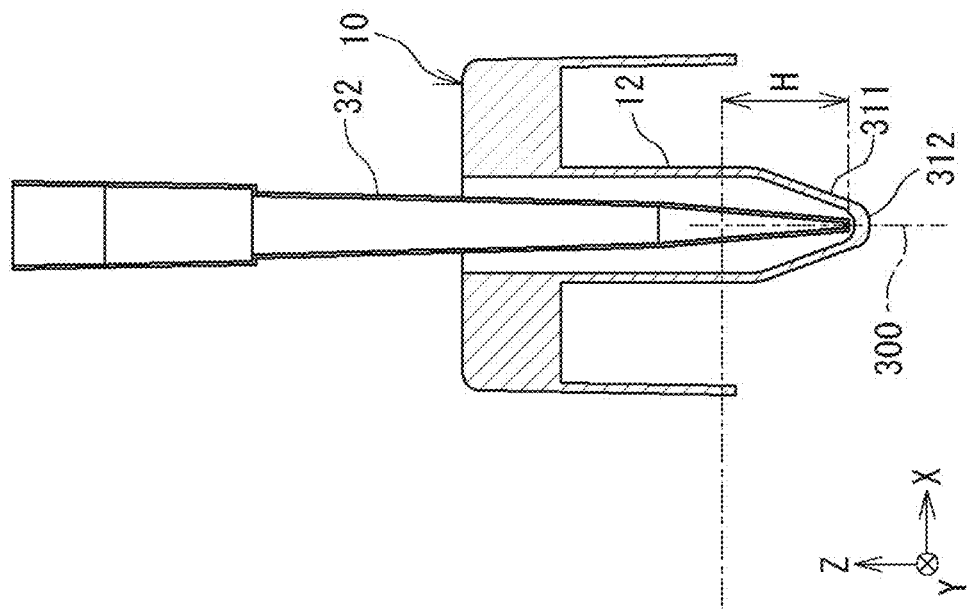
FIGS. 11A and 11B are illustrations of a discharge position and a suction position.
Figure 11A:
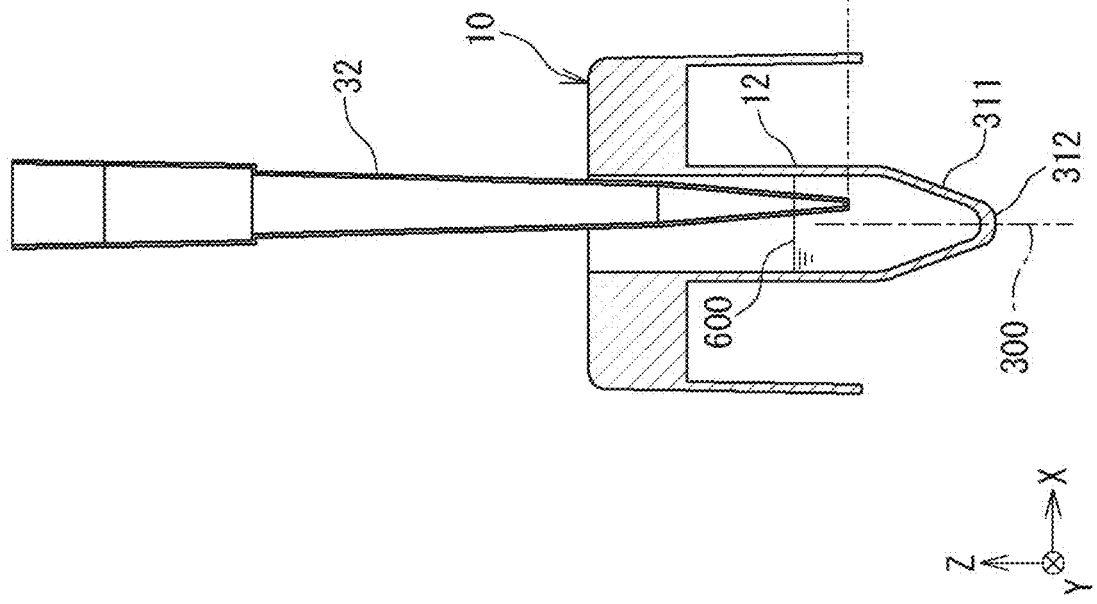

FIG. 11 shows the discharge position (see FIG. 1A) of the pipette tip 32 (nozzle) at the time of each discharge for dispersing the magnetic particles 500, and the suction position (FIG. 1B) of the pipette tip 32 when suctioning between each discharge. As shown in FIG. 11A and FIG. 11B, the discharge position shown in FIG. 11A is higher by height H than the suction position shown in FIG. 11B. In other words, the suction position shown in FIG. 11B is lower than the discharge position shown in FIG. 11A. In order to sufficiently suction the liquid in the second reaction tank 12, the suction position is preferably in the vicinity of the bottom of the second reaction tank 12, and the lower the suction position, the more liquid can be suctioned.

In order to make the suction position as low as possible, it is preferable to position the pipette tip 32 (nozzle) at the center of the container 12 (the position of the central axis 300). However, if the liquid can be sufficiently suctioned, the pipette tip 32 may be positioned in a range 301 directly above the inclined part on the side opposite the particles 500 with the central axis 300 of the container 12 in between. In this case, the discharge position and the suction position are the same or proximate to each other, and the transport amount of the pipette tip 32 when repeating discharge and suction can be reduced. Note that transfer of the pipette tip 32 when repeated discharge and suction are performed is controlled by the control unit 405 which controls the transfer parts 143, 144, 145.

As shown in FIG. HA, the discharge position is such that the tip of the pipette tip 32 is below the liquid surface 600 of the discharged liquid, and preferably is a position where it is immersed in the liquid after completion of one discharge. There is concern of wasting a part of the discharged reagent that adheres to the inner surface of the container above the liquid surface 600 if the tip of the pipette tip 32 is positioned above the liquid level 600 of the discharged liquid; however, if the tip of the pipette tip 32 is below the liquid surface 600 of the discharged liquid, the entire amount of the discharged reagent is used for dispersing the particles.

When discharging the reagent from the pipette tip 32, the discharge position is preferably a position where the pipette tip 32 does not contact the inner surface of the second reaction tank 12 as shown in FIG. 11A. When the pipette tip 32 comes into contact with the inner surface of the second reaction tank 12, there is a possibility that the pipette tip 32 will detach since the pipette tip 32 is detachable from the suction part 141 and is not rigidly mounted. In order to prevent detachment, it is preferable that the discharge position is such that the pipette tip 32 does not contact the inner surface of the second reaction tank 12.

Each discharge position may be the same position, but is preferably a different position. It is preferable that each discharge position is different in the circumferential direction of the second reaction tank 12. For example, in step S201, the particles 500 can be peeled off in a wide range in the circumferential direction by making the first discharge position in the first discharge different from the second discharge position in the second discharge in step S203. As described above, the flow formed by the tapered bottom container 12 has a strong directivity and locally generates high shear stress. Therefore, in order to peel off a wide range of particles 500, it is preferable to change the discharge position in the circumferential direction.

Figure 12:
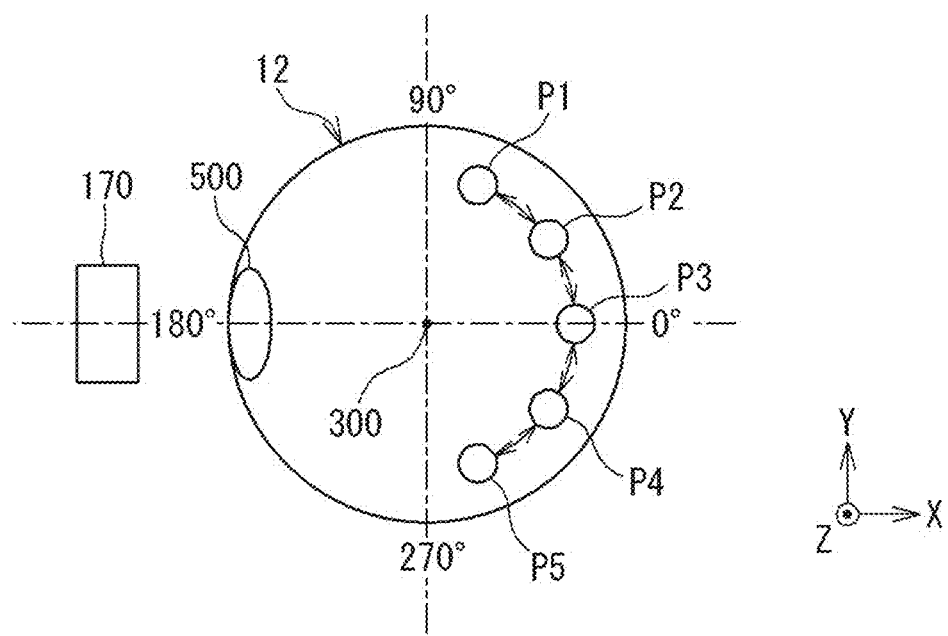
FIG. 12 is an illustration of a discharge position.

The different discharge positions in the circumferential direction can be, for example, positions P1, P2, P3, P4, P5 shown in FIG. 12. P1, P2, P3, P4, and P5 are set in the range 301 which is on the side opposite the particles 500 relative to the central axis 300 of the second reaction tank 12 and is directly above the inclined part. These discharge positions P1, P2, P3, P4, P5 can be set, for example, at intervals of 30° in the circumferential direction, but are not limited to 30° increments, and may be, for example, 15° increments. The discharge position can be appropriately set in a range from 0° to 90°, and a range from 0° to 270° in FIG. 12.

According to the analyzer 100 of the embodiment, particularly remarkable effects can be obtained with respect to particle dispersion in the case where the preparation of the measurement sample is automated. That is, the area where the magnetic particles are fixed to the container is not the same each time inasmuch as there is a variation. In the case of dispersing the magnetic particles fixed by human hand, it is possible to appropriately adjust the region to which the liquid is sprayed according to the variation, but it is difficult to perform the dispersion process according the variations when a measurement sample is prepared automatically as in the analyzer 100 of the embodiment. For example, although providing a camera for identification may be considered in order for the analyzer to identify the fixing region and the fixing state of the magnetic particles, there are the problems of increased size and increased cost of the analyzer. On the other hand, according to the analyzer 100 of the embodiment, shearing forces can be applied to the fixed region of the magnetic particles for a long time with a stronger force, so even if there are variations to some extent in the region where the magnetic particles are fixed, it is possible to efficiently disperse the magnetic particles and obtain a particularly remarkable effect when automating the preparation of the measurement sample.

3. Conditions Suitable for Particle Dispersion

Returning to FIG. 10, the reagent is discharged from the nozzle 32 located in the container (second reaction tank) 12 in the particle dispersion method of the embodiment. The particles 500 are fixed to the inner surface of the container 12 by attraction with the magnet 170. By discharging the reagent, the particles 500 fixed to the container 12 are peeled off, and the particles 500 are dispersed in the reagent. The particles 500 are, for example, magnetic particles that affix a target substance. The target substance is, for example, a nucleic acid. The magnetic particles fixed to the inner surface of the container 12 may affix the target substance or may not affix the target substance.

As shown in FIG. 10A, the container (second reaction tank) 12 has an inclined part 311 on the bottom side of the cylindrical body part 310. The inclined part 311 tapers toward the bottom side of the container 12. The inner diameter of the inclined part 311 relative to the central axis 300 of the container 12 changes linearly in the direction of the central axis 300. In the inclined part 311, the angle is constant relative to the central axis 300.

In the embodiment, the container 12 includes a rounded bottom 312 on the far bottom side of the inclined part 311. In this way, the bottom part 312 of the container 12, which is the tapered tip, has a rounded shape. The shape of the bottom part 312 may be, for example, a spherical shape or an ellipsoidal shape. In the following description, it is assumed that the bottom part 312 is spherical. Note that the bottom part 312 also may have a pointed shape.

As shown in FIG. 10A, the particles 500 are fixed, for example, on the inclined part 311. The fixing range of the particles 500 may extend from the inclined part 311 to the main body part 310.

At the time of discharge, the nozzle 32 is located in a range opposite to the particles 500 with the central axis 300 in between. As shown in FIG. 10B, that is, in plan view of the container 12, the nozzle 32 can be positioned, for example, on a straight line passing through the center of the fixing range of the particles 500 and the central axis 300. In FIG. 10B, the position of the nozzle 32 in the circumferential direction is indicated as 0°, and the position of the particles 500 is shown as 180°. The range on the side opposite the particles 500 from the central axis 300 is not limited to the 0° position, and may be in the range from 0° counterclockwise to 90° and from 0° clockwise to 270°.

In FIG. 10B, the fixing range of the particles 500 is a part in the circumferential direction of the container 12, and more specifically, is the vicinity of 180° shown in FIG. 10B. The range of positioning the nozzle 32 therefore is from 0° counterclockwise to 90° and from 0° clockwise to 270°, which is the non-adhesion range of the particles 500. Since the particles 500 are preferably locally fixed in the container 12 in order to efficiently peel off the fixed particles 500, the non-fixing range of the particles 500 in the circumferential direction of the container 12 is preferably in a range of at least half circumference (a range of) 180°, and more preferably in a range of at least 270°. In other words, the fixing range of the particles 500 is preferably 180° or less, more preferably 120° or less, and even more preferably 90° or less in the circumferential direction of the container.

At the time of discharge, the nozzle 32 is located directly above the inclined part 311. Directly above the inclined part 311 does not include the position of the central axis 300 which is immediately above the tapered tip. In the case where the tapered tip 312 has a rounded shape, since the rounded region 303 is not an inclined part having a constant inclination angle, "directly above the inclined part 311" means a range 301 and 302 within the container 12 excluding the rounded region 303, respectively. When the tapered tip 312 has a spherical shape as in FIG. 10, the radial distance x from the central axis 300 from the central axis to the boundary between the range 303 and the ranges 301 and 302 is set such that the angle θ of the inclined part and the radius of curvature R of the rounded part can be expressed by R cos θ. Note that the linear taper is simply referred to as a taper, and in the case of a taper, it does not include a shape having roundness.

4. First Simulation: Shear Stress Distribution Changes Over Time

Figure 13:
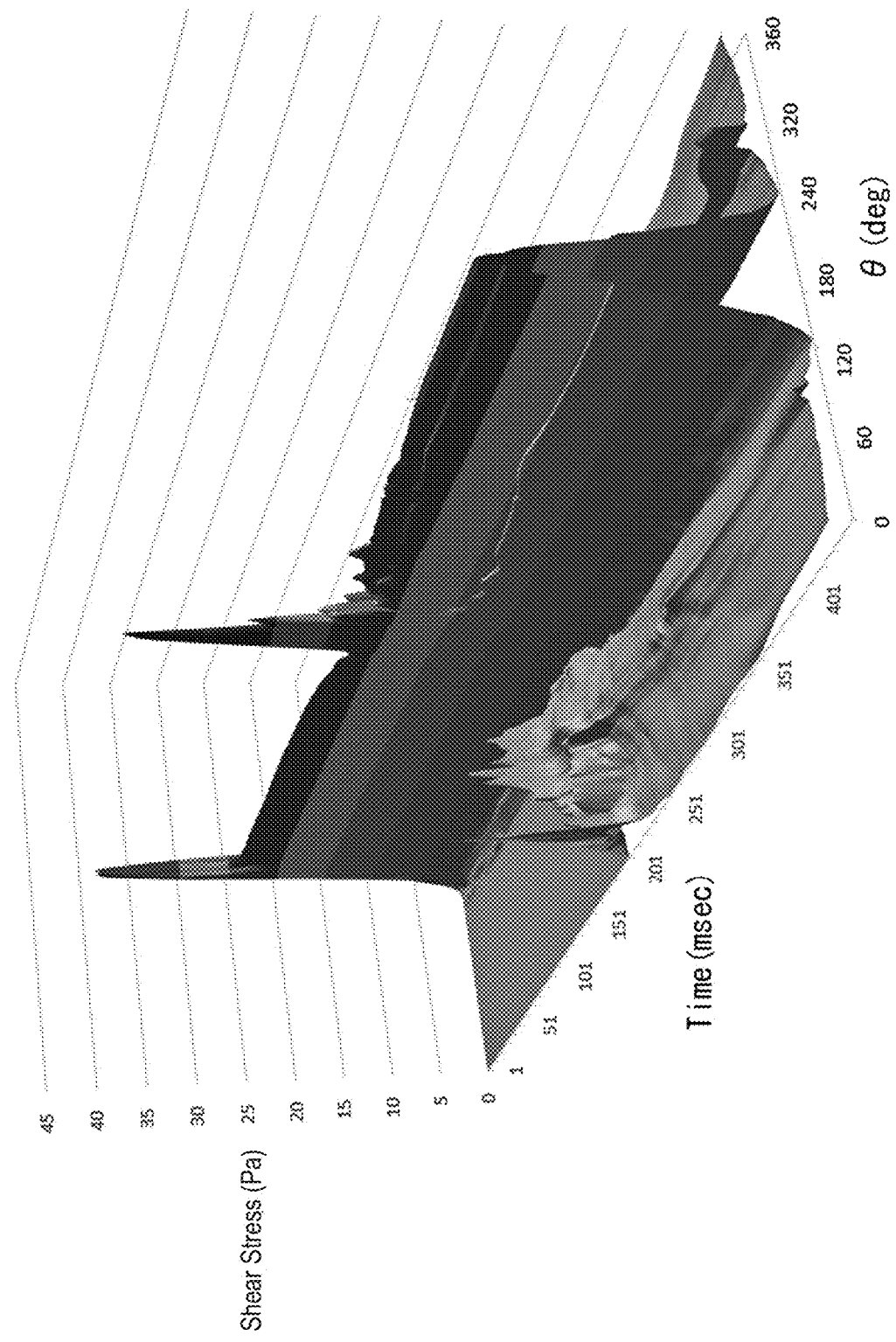
FIG. 13 is a diagram showing the change over time in shear stress distribution.
Figure 14:
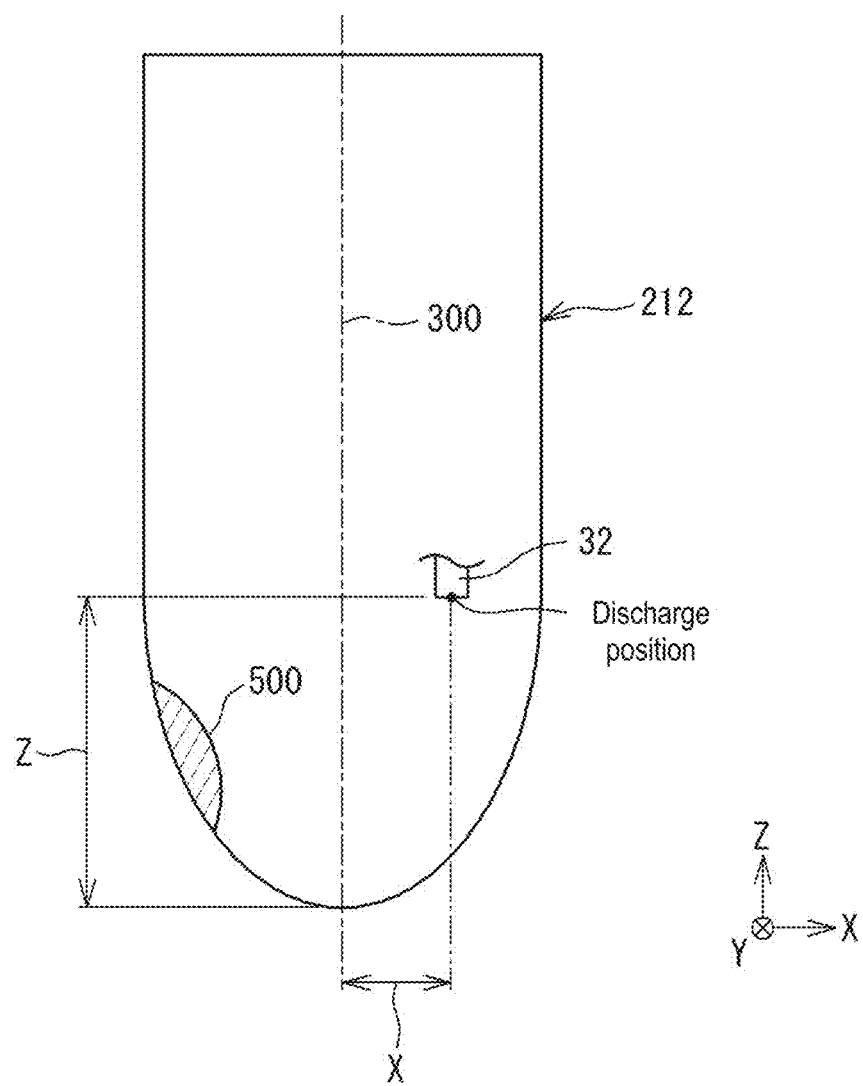
FIGS. 14A and 14B are illustrations of particle dispersion according to a comparative example.
Figure 14:
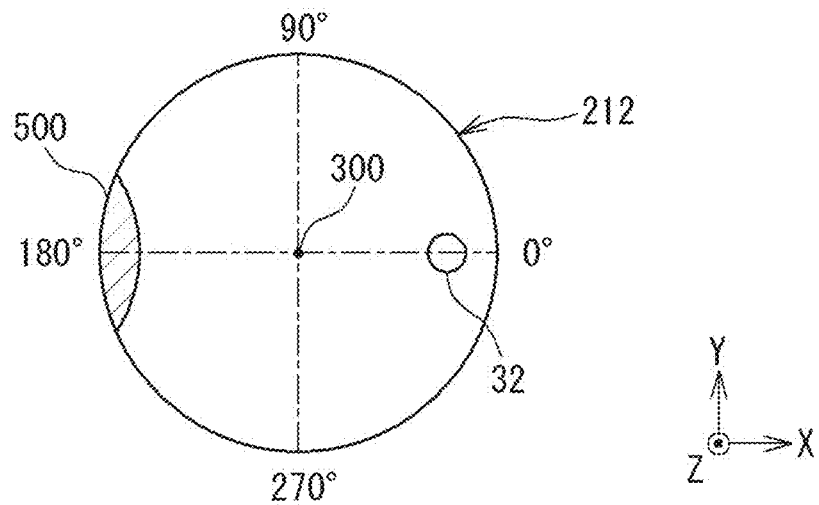

In the first simulation, the influence of the shape of the container on the shear stress caused by the fluid was examined. FIG. 13 shows simulation results for the container (tapered bottom container; second reaction tank) 12 having the inclined part shown in FIG. 10, and FIG. 15 shows the simulation results for the ellipsoidal bottom container 212 shown in FIG. 14.

In the simulation shown in FIG. 13, the angle θ of the inclined part in the tapered bottom container 12 is 20°, and the radius of curvature R of the rounded tapered tip 312 is 1.75 mm. The discharge position from the nozzle 32 has a height z of 5 mm from the bottom of the container 12 and a radial distance x of 1.5 mm from the central axis 300. Note that the diameter of the container 12 was 10 mm.

Figure 15:
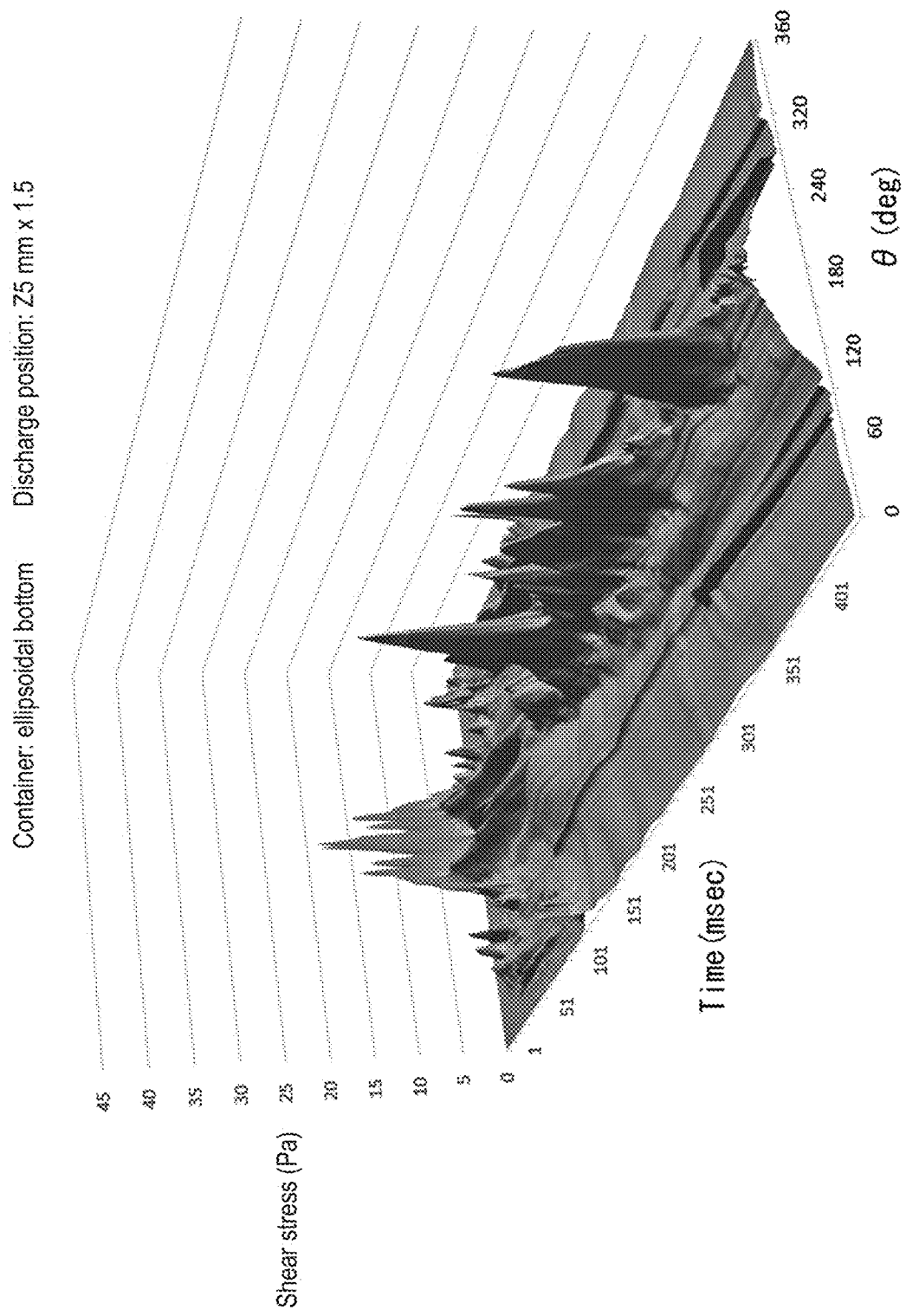
FIG. 15 is a diagram showing the change over time in shear stress distribution.

In the simulation shown in FIG. 15, the ellipsoidal bottom container 212 is an ellipsoid with a bottom part having the long axis direction in the direction of the central axis 300, and its long radius is 8.5 mm. The discharge position from the nozzle 32 has a height z of 5 mm from the bottom of the container 12 and a radial distance x of 1.5 mm from the central axis 300.

The simulation results shown in FIG. 13 and FIG. 15 show changes over time of the shear stress distribution at the position where the height from the bottom of the containers 12 and 212 is 5 mm. The shear stress distribution is the distribution in the circumferential direction of the containers 12 and 212 and, in FIG. 13 and FIG. 15, θ=0° is the position (discharge position) of the nozzle 32, and θ=180° is the position of the particles 500. The analysis time is during the 0.45 seconds from the discharge start to the end. Note that there is no liquid in the containers 12 and 212 before the start of discharge.

As shown in FIG. 13, in the tapered bottom container 12, shear stress is intensively generated with a high directivity focused at the position of θ=180° on the opposite side of the nozzle 32, such that high shear stress can be stably generated over time. Very high shear stress also is instantaneously obtained immediately after discharge and in the middle stage of discharge. Therefore, in the tapered bottom container 12, the particles 500 can be peeled from the container 12 by high shearing stress even when the particles 500 are firmly fixed to the container 12.

On the other hand, as shown in FIG. 15, in the ellipsoidal bottom container 212, the relative shearing stress is small, and unstable shearing stress is generated in a relatively wide range centered on θ=180°, the directivity is low, and the strength of shear stress is unstable even over time. When the particles 500 are strongly fixed to the container 12, the particles 500 may not be separated from the container 12 by such a shear stress regardless of how many times the reagent is discharged.

5. Second Simulation: Stream Line Vector

In the second simulation, the influence of the shape of the container on the flow of the solution was verified by streamline vector analysis. FIG. 16 to FIG. 19 show the results of the second simulation, and the numerous arrows in the figure are streamline vectors showing the flow of the fluid discharged from the nozzle 32. Note that the simulation conditions in the second simulation are the same as those in the first simulation. In FIG. 16 to FIG. 19, A shows a sectional view of the tapered bottom container 12, B shows a plan view of the tapered bottom container 12 (position of height z=5 mm), C shows a cross-sectional view of the ellipsoidal bottom container 212, and D a plan view of the ellipsoidal bottom container 212 (position of height z=5 mm).

FIG. 16 shows the flow of the solution immediately after discharge of the solution (0.01 second after the start of discharge). As shown in FIG. 16A, in the case of the tapered bottom container 12, when the solution discharged downward from the nozzle 32 positioned on the side opposite the particles 500 strikes the inclined part 311 directly under the nozzle 32, the solution transits the container bottom part 312 and ascends the inclined part 311 on the particles 500 side. In FIG. 16A, the solution forms a thin layer and rises on the inner surface of the container 12. In the case of the tapered bottom container 12, since the crossing angle θ between the nozzle 32 and the inclined part 311 is relatively small, the kinetic energy loss of the solution is small and the solution rises to a higher position. In the tapered bottom container 12, the shear stress immediately after discharge was 27.7 Pa.

Figure 16A:
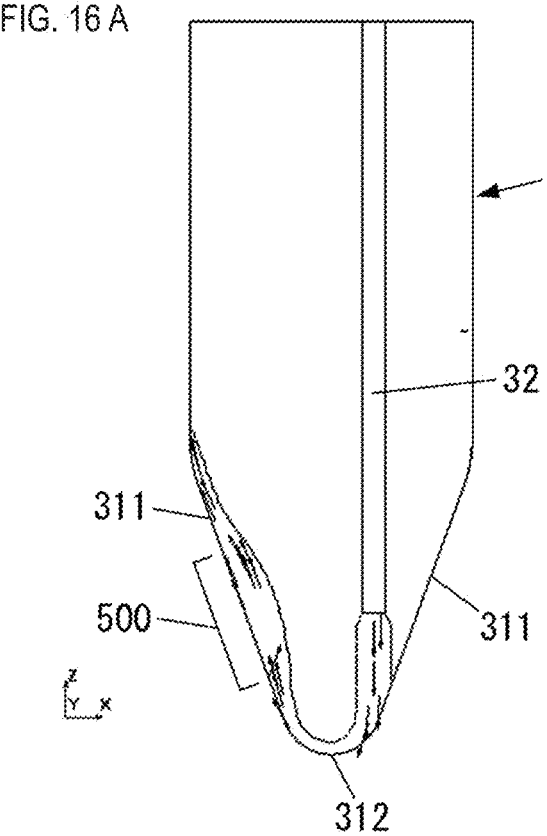
FIGS. 16A through 16D are vector diagrams of discharge fluid.
Figure 16B:
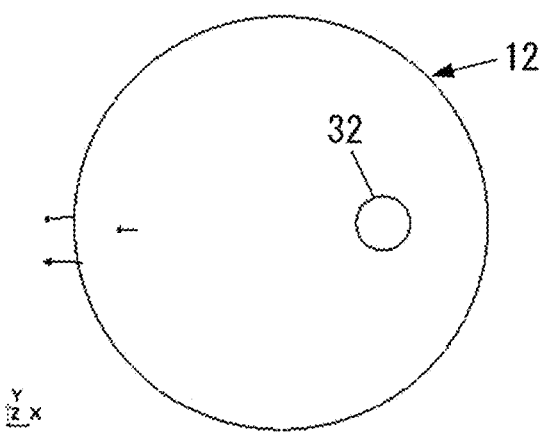
Figure 16C:
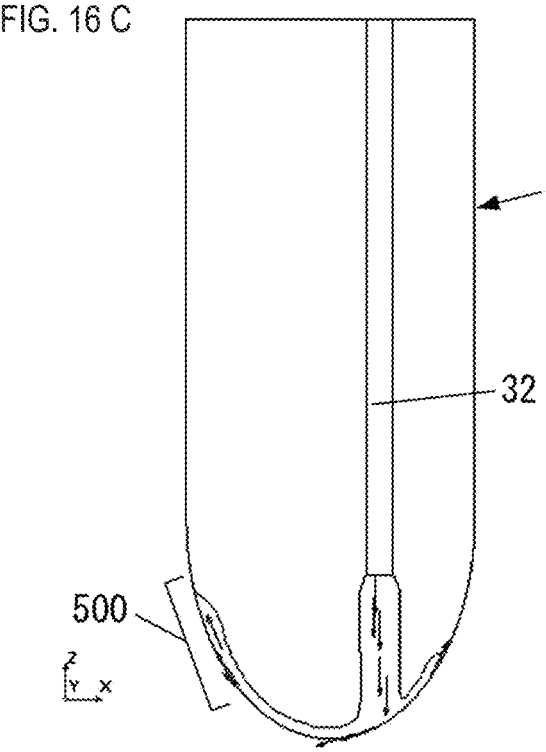
Figure 16D:
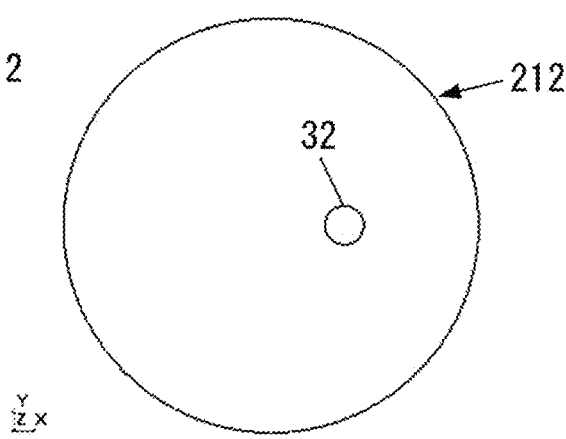

On the other hand, in the case of the ellipsoidal bottom container 12 shown in FIG. 16C, when the solution discharged downward from the nozzle 32 positioned on the side opposite the particles 500 strikes the ellipsoidal surface directly under the nozzle 32, the solution transits the bottommost part of the container and ascends the ellipsoidal surface on the particles 500 side on the particles 500 side. In FIG. 16C, the solution forms a thin layer and rises on the inner surface of the container 12. However, in the case of the ellipsoidal bottom container 212, since the crossing angle between the nozzle 32 and the ellipsoidal surface is relatively large, kinetic energy loss occurs and the solution speed decreases when the solution strikes the container 212. A flow not directed to the particles 500 also is generated, thus increasing the loss. In the ellipsoidal bottom container 212, the shear stress immediately after discharge was 19.7 Pa.

FIG. 17 shows the flow of the solution in the initial discharge of the solution (0.01 second after the start of discharge). In the case of the tapered bottom container 12 as shown in FIG. 17A, the solution ascends to a position sufficiently higher than the particles 500, and a retention locus can be formed at a position distant from the particles 500. At the location where the particles 500 are aggregated, a thin layer flow continues to be formed and a high shear stress is maintained. In the tapered bottom container 12, the shear stress at initial discharge was 24.2 Pa.

On the other hand, in the case of the ellipsoidal bottom container 212 as shown in FIG. 17C, the upward flow collides with the downward flow due to gravity, and a retention locus occurs near the aggregation point of the particles 500. The shear stress acting on the particles 500 decreases due to the retention. It is presumed that the decrease in shear stress is caused by loss of kinetic energy and separation of flow (the flow away from the inner wall of the container) due to the shape of the container 212. In the ellipsoidal bottom container 212, the shear stress at initial discharge was 6.4 Pa.

FIG. 18 shows the flow of the solution at the middle stage of solution discharge (0.214 seconds from the start of discharge and 0.205 seconds from the start of discharge of the tapered bottom container). At the location where the particles 500 are aggregated, a thin layer flow continues to be formed and a high shear stress is maintained as shown in FIG. 18A. Since the kinetic energy of the solution is high, the retention locus is formed at a position sufficiently higher than the particles 500. In the taper container 12, the shear stress at the middle stage of discharge was 42.9 Pa, the maximum shear stress generated.

In the ellipsoidal bottom container 212, the shear stress also was 24.9 Pa at the middle stage of discharge, the maximum shear stress generated. However, the reason a large shear stress occurred is that a thin laminar flow was inadvertently formed at the location of aggregated particles 500 due to the bubbles taken into the liquid as shown in FIG. 18C. Since the formation of bubbles is random, the occurrence of high shear stress is a phenomenon with low reproducibility in the ellipsoidal bottom container 212. Further, as shown in FIG. 18D, the flow towards the nozzle 32 increases, and the loss of kinetic energy acting on the particles 500 occurs.

Figure 19:
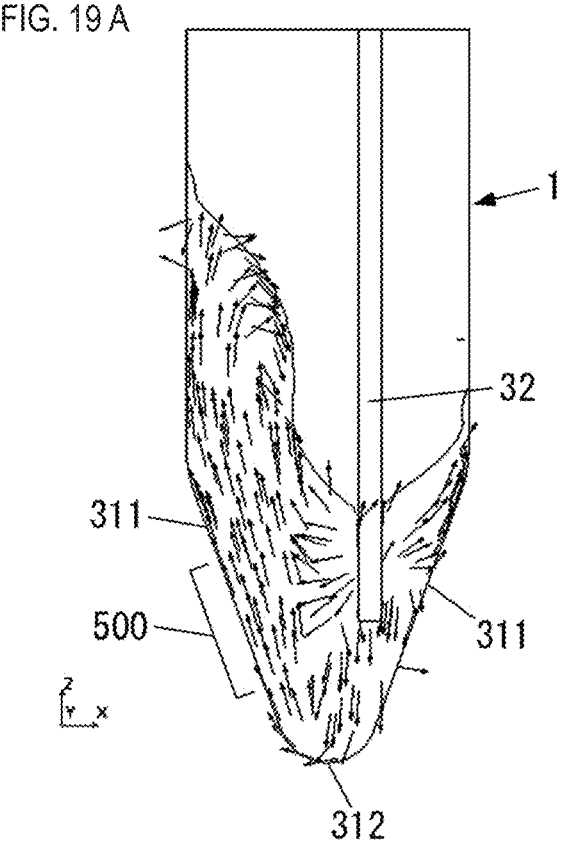
FIGS. 19A through 19D are vector diagrams of discharge fluid.
Figure 19:
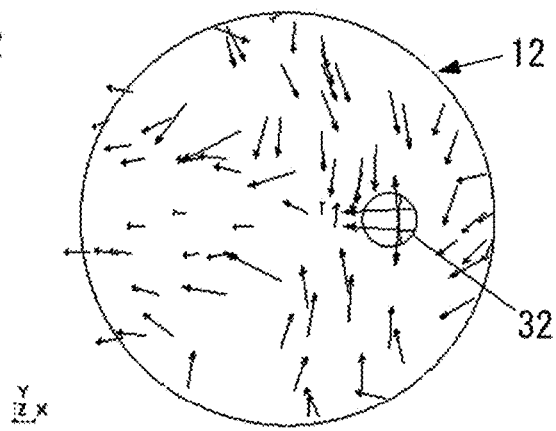
Figure 19:
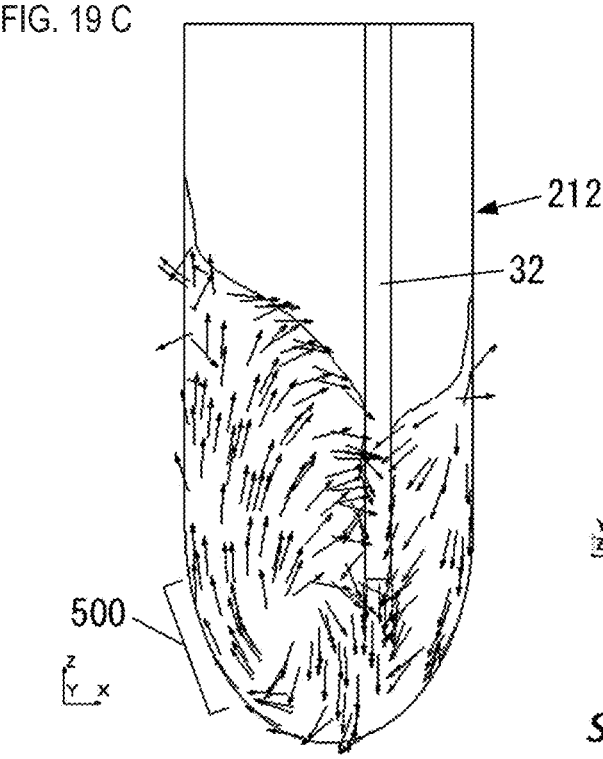
Figure 19:
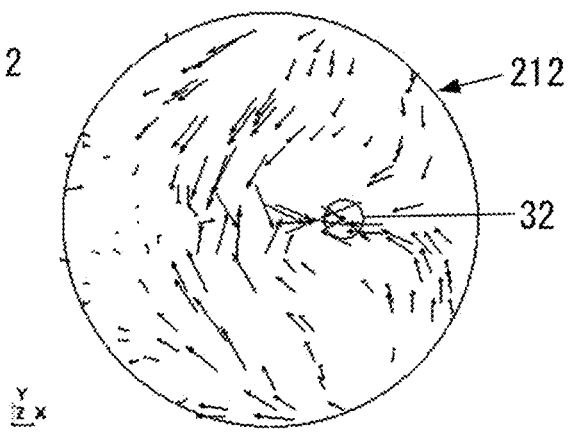
Figure 21:
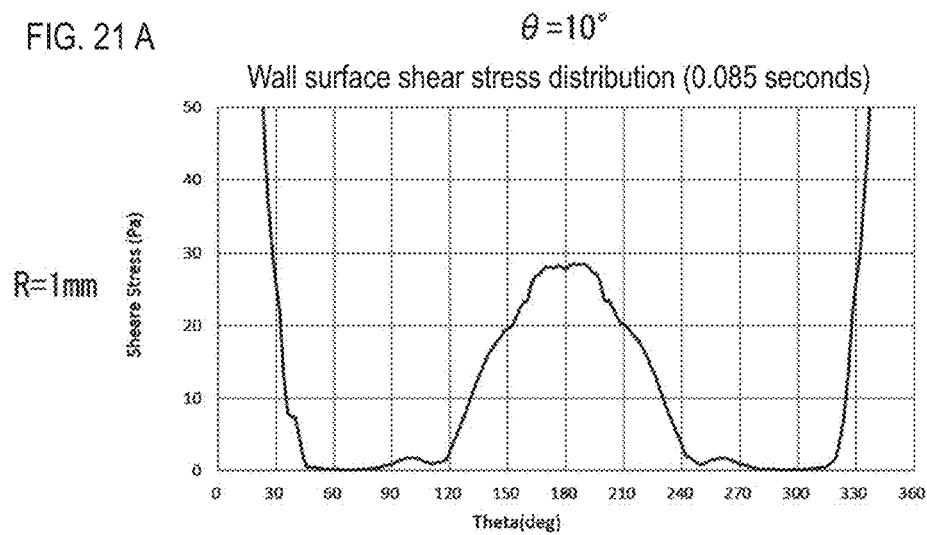
FIGS. 21A and 21B are shear stress distribution charts.
Figure 21:
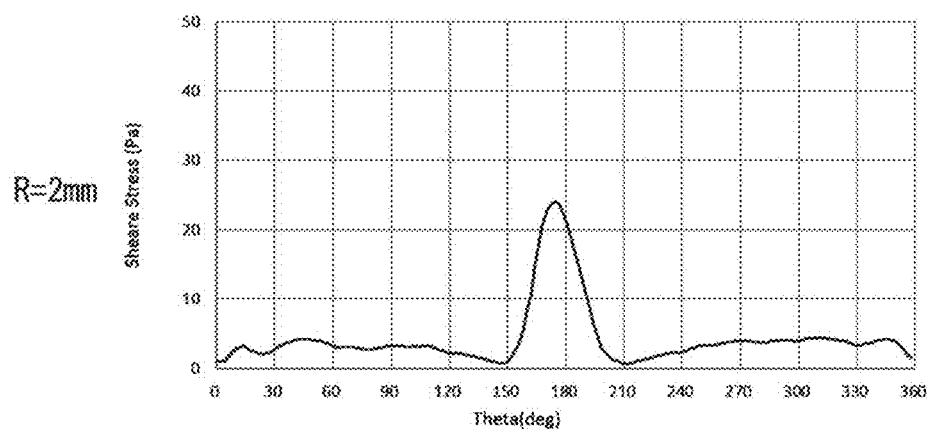
Figure 22:
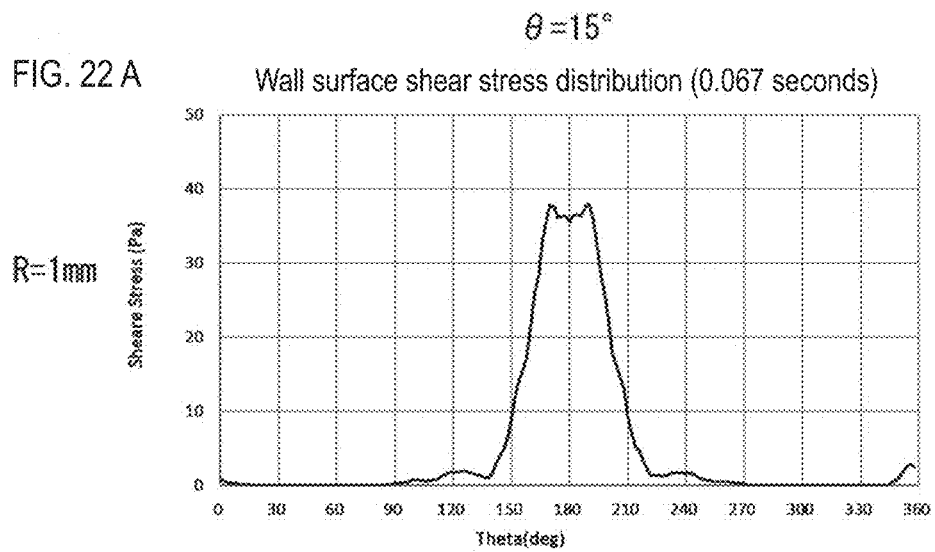
FIGS. 22A through 22C are shear stress distribution charts.
Figure 22:
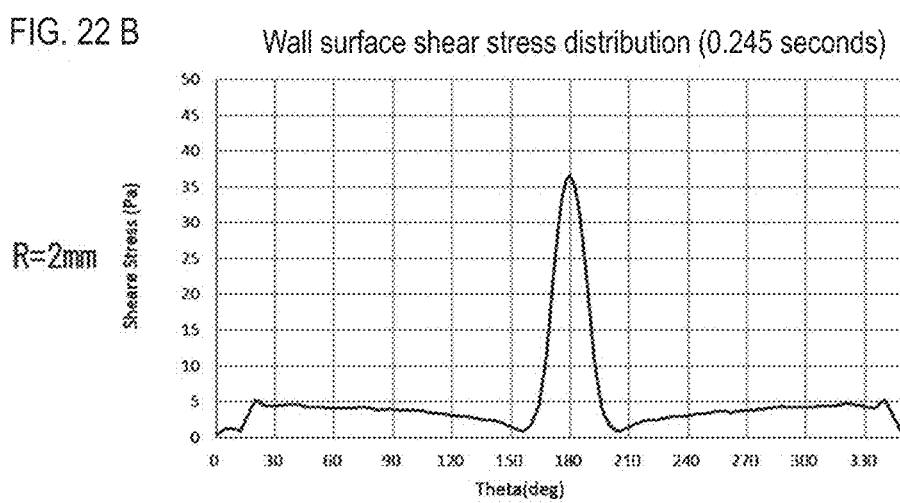
Figure 22:
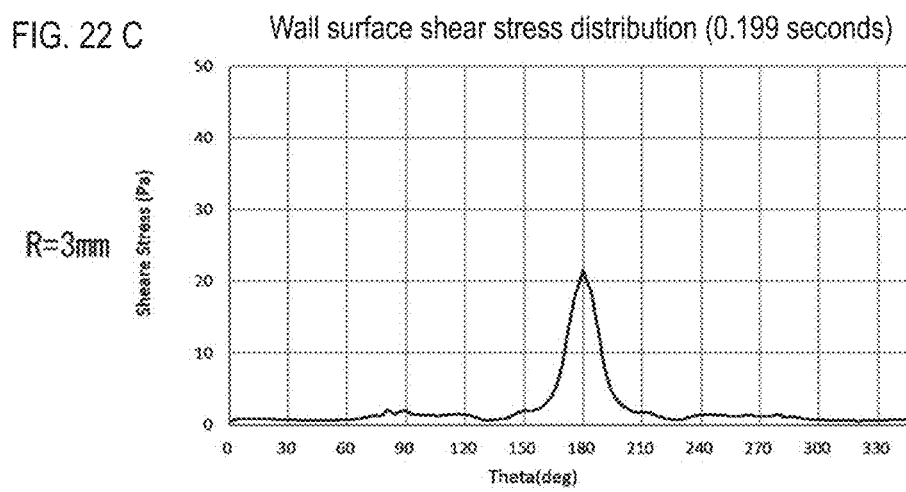
Figure 23:
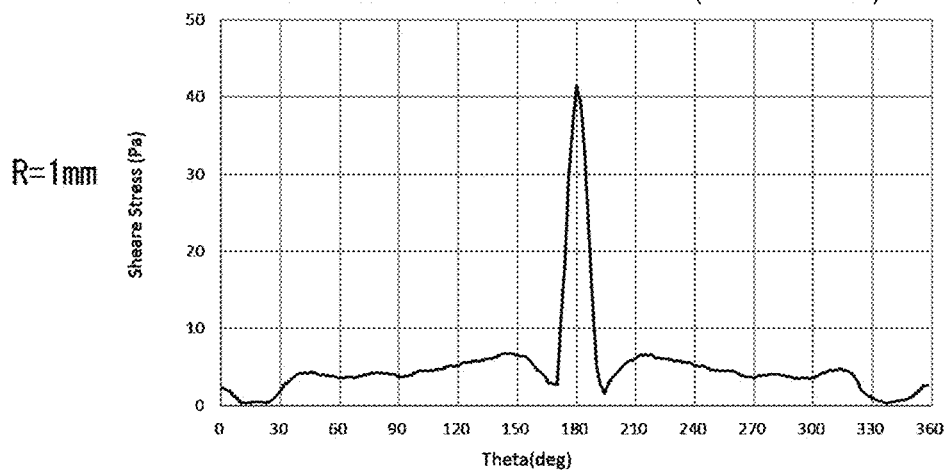
FIGS. 23A through 23C are shear stress distribution charts.
Figure 23:
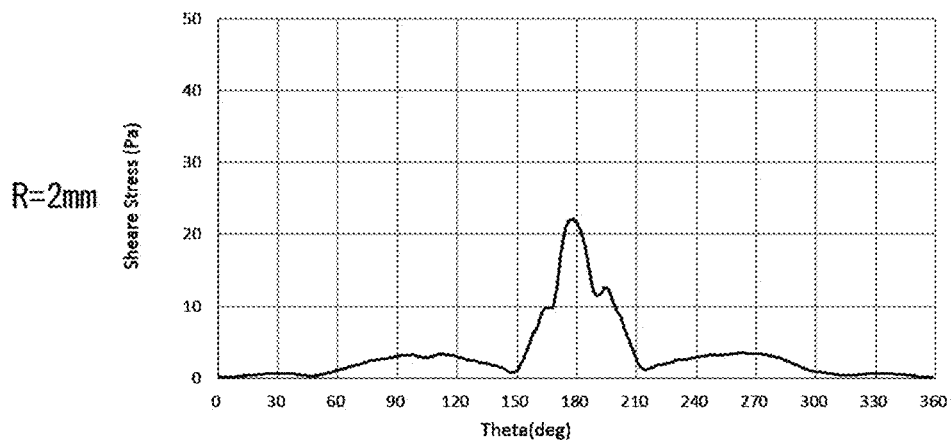
Figure 23:
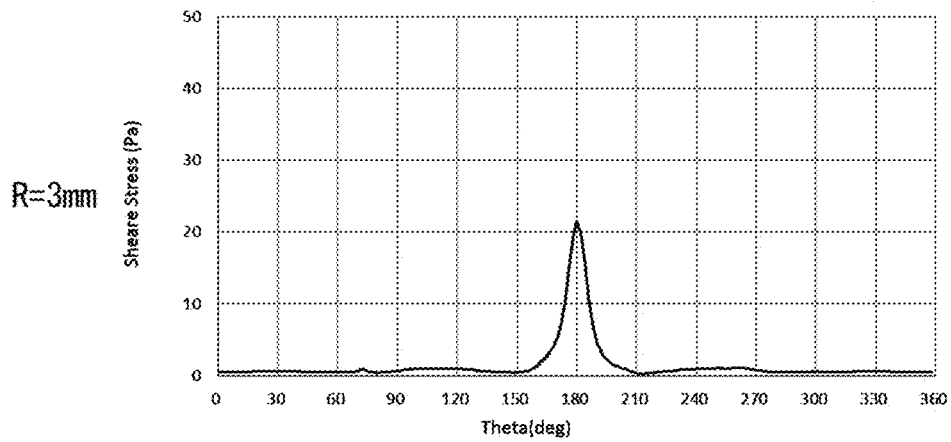
Figure 24:
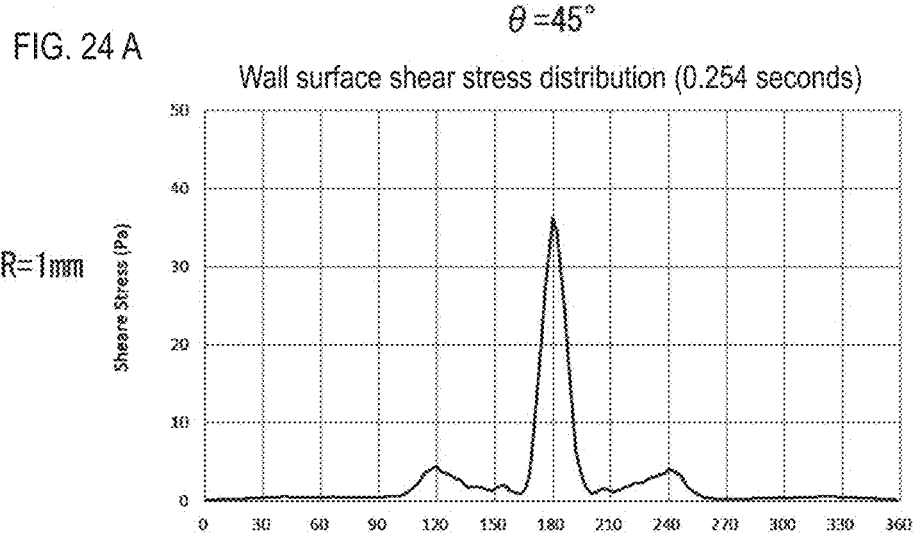
FIGS. 24A through 24C are shear stress distribution charts.
Figure 24:
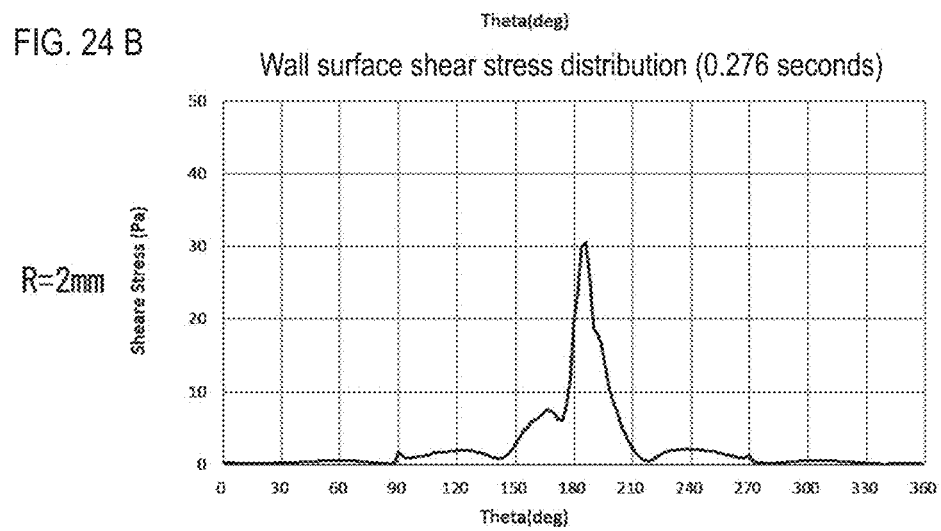
Figure 24:
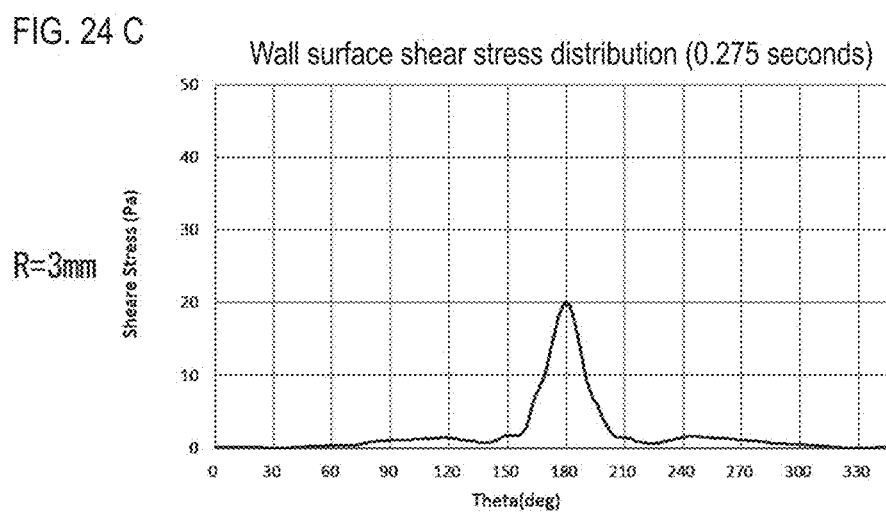
Figure 25:
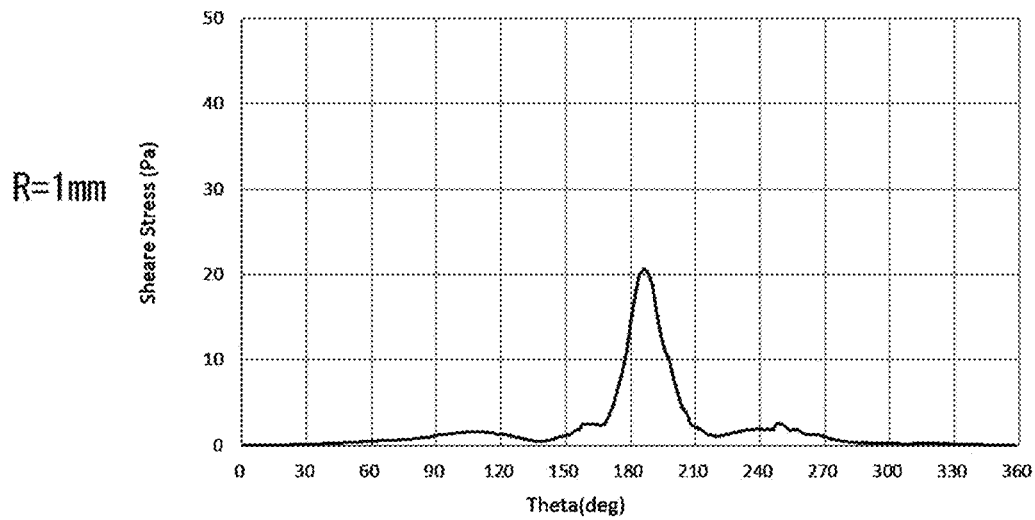
FIGS. 25A through 25C are shear stress distribution charts.
Figure 25:
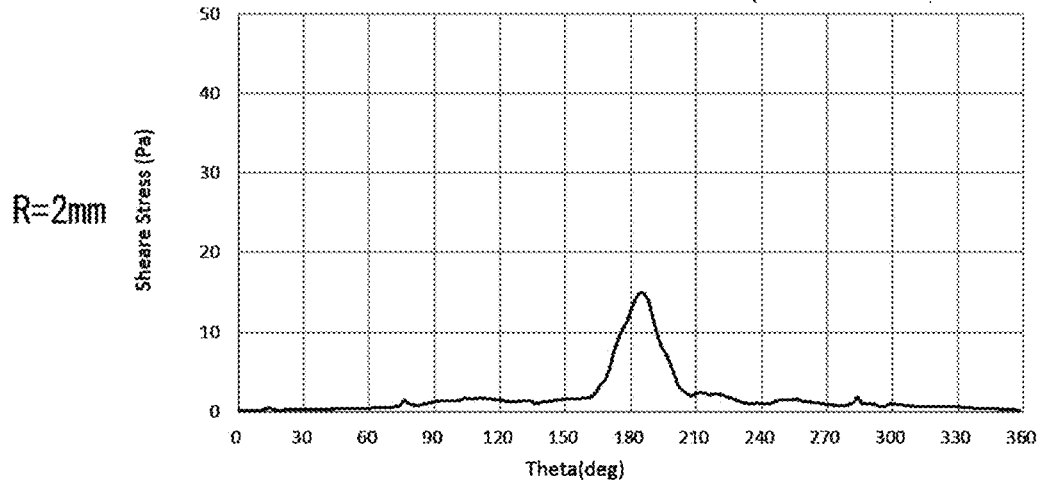
Figure 25:
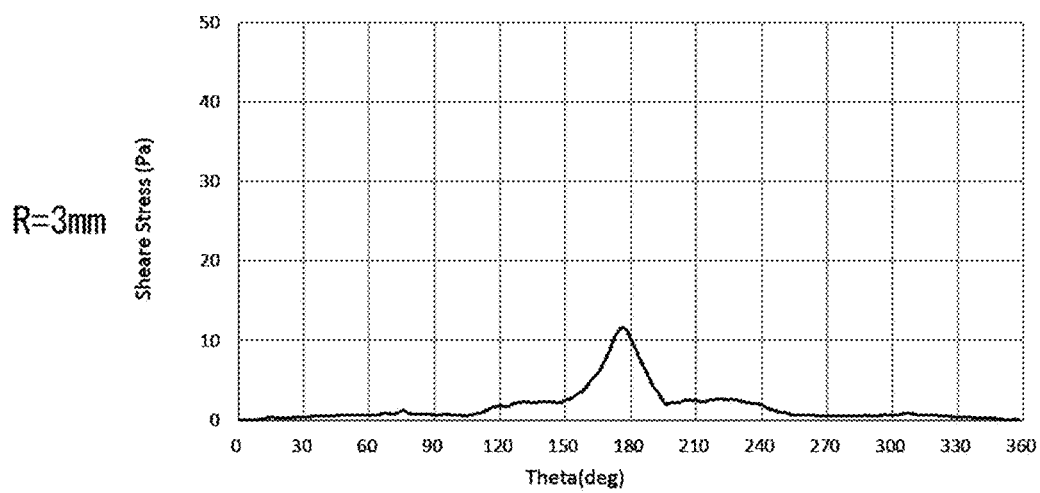

FIG. 19 shows the flow of the solution at the latter stage of discharge of the solution (0.45 second after the start of discharge). In the case of the tapered bottom container 12 As shown in FIG. 19A, a fast flow is formed at the aggregated location of the particles 500 even in the latter period of discharge, and high shearing stress is generated. In the tapered bottom container 12, the shear stress at the late stage of discharge was 25.5 Pa.

On the other hand, in the case of the elliptical bottom container 212 as shown in FIG. 19C, the solution forms a longitudinal vortex (tumble flow) in the container 212. A gentle flow is formed at the aggregated location of the particles 500, and the shear stress is low. In the ellipsoidal bottom container 212, the shear stress at the late stage of discharge was 6.5 Pa.

As described above, in the case of the tapered bottom container 12, it is possible to stably generate a high shear stress from immediately after discharge to the late stage of discharge, maintain high kinetic energy and normally produce a fast flow at the aggregation location of the particles 500. Further, in the case of the tapered container 12, the retention locus is formed at a position higher than the particles 500, and reduction of the shear stress is easily avoided. In the case of the tapered bottom container 12, the solution tends to flow along the tapered shape, so that it is thought that the flow does not separate from the container 12 and forms no vortex in the container 12. The formation of a vortex is a factor of lowering the shear stress according to comparison with the ellipsoidal bottom container 212. Further, in the case of the tapered bottom container 12, it is possible to form a stable flow over time since bubbles are unlikely to become entrapped.

Conversely, in the case of the ellipsoidal bottom container 212, an unstable shear stress is generated over time, and the shear stress as a whole is low compared with the tapered bottom container 12. Kinetic energy loss also occurs because the direction of discharge from the nozzle and the inner wall of the container are close to right angles. In the case of the ellipsoidal container 212, the flow advancing along the inner wall of the container 212 separates from the container forming a vortex (tumble flow) and forming a flow that easily entraps bubbles, which results in an unstable flow over time.

6. Third simulation: Variation of the Taper Angle $\theta$ and the Curvature Radius R of the Bottom In the third simulation, in the tapered bottom container 12 shown in FIG. 10, the shear stress distribution was obtained by making the taper angle $\theta$ and the curvature radius R of the bottom part different. Simulation conditions other than $\theta$ and R were the same as in the first simulation.

FIG. 20 to FIG. 25 show the results of the third simulation. FIG. 20 to FIG. 25 show shear stress distributions at a position where the height from the bottom of the container 12 is 5 mm. The shear stress at each point in time is as shown in the drawings.

FIG. 20A shows a case in which $\theta=5°$ and R=1 mm. FIG. 20B shows a case in which $\theta=5°$ and R=2 mm.

FIG. 21A shows a case in which $\theta=10°$ and R=1 mm. FIG. 21B shows a case in which $\theta=10°$ and R=2 mm.

FIG. 22A shows a case in which $\theta=15°$ and R=1 mm. FIG. 22B shows a case in which $\theta=15°$ and R=2 mm. FIG. 22C shows a case in which $\theta=15°$ and R=3 mm.

FIG. 23A shows a case in which $\theta=30°$ and R=1 mm. FIG. 23B shows a case in which $\theta=30°$ and R=2 mm. FIG. 23C shows a case in which $\theta=30°$ and R=3 mm.

FIG. 24A shows a case in which $\theta=45°$ and R=1 mm. FIG. 24B shows a case in which $\theta=45°$ and R=2 mm. FIG. 24C shows a case in which $\theta=45°$ and R=3 mm.

FIG. 25A shows a case in which $\theta=60°$ and R=1 mm. FIG. 25B shows a case in which $\theta=60°$ and R=2 mm. FIG. 25C shows a case in which $\theta=60°$ and R=3 mm.

Evaluations of the third simulation results shown in FIG. 20 to FIG. 25 are shown in Table 1 below.

TABLE 1

| | | $\theta°$ | | | | | |
| --- | --- | --- | --- | --- | --- | --- | --- |
| | | 5° | 10° | 15° | 30° | 45° | 60° |
| Rmm | 1 mm | C2 | B2 | B1, B2 | B2 | B2 | C1 |
| | 2 mm | A | A | A | A | A | A |
| | 3 mm | — | — | C1 | C1 | C1 | C1 |

The definitions of A, B1, B2, C1 and C2 in Table 1 are as follows. A indicates a result of very good from the viewpoint of the magnitude of the shearing stress and its stability over time. B1 indicates a result in which liquid leakage from the container 12 was observed although the magnitude of the shear stress and its stability over time were good. B2 indicates that liquid splash occurred although the magnitude of the shear stress and its stability over time were good. C1 indicates that the shear stress was relatively smaller than A, B1, B2. C2 indicates that the shear stress was relatively smaller than A, B1, B2, and that the flow towards the particles 500 was also relatively smaller than A, B1, B2.

According to the third simulation results, the radius of curvature R of the rounded end of the tapered tip 312 can be 1 mm or more. The radius of curvature R also can be 3 mm or less, and preferably 2 mm or less. The radius of curvature R is preferably 2 mm. In the case where the roundness of the tapered tip 312 is not a spherical shape, the radius of curvature R of a circle contacting an arbitrary point in the roundness may be the above-mentioned numerical value.

According to the third simulation results, the taper angle $\theta$ can be 5° or more, and is preferably 10° or more. The taper angle $\theta$ also can be 60° or less, preferably 45° or less, and more preferably 30° or less.

7. Fourth Simulation: Variation of Discharge Position (X-Axis Direction)

Figure 3:
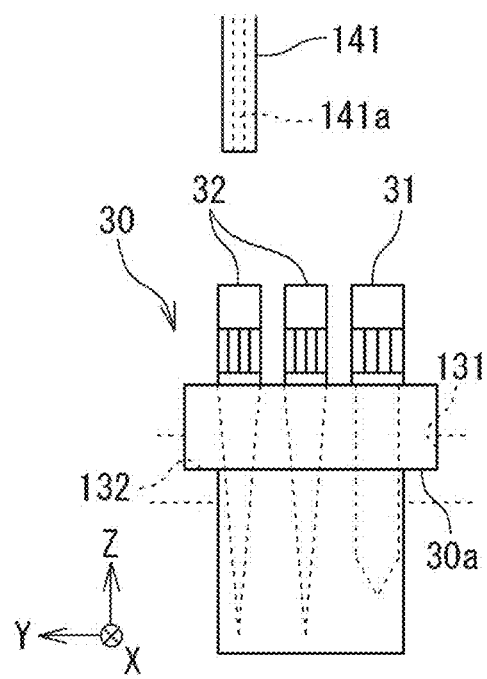
FIG. 3A is schematic views of a second container and a suction part.
FIG. 3B is schematic views of a second container and a suction part.
FIG. 3C is a schematic diagram of a dispensing unit.
Figure 3:
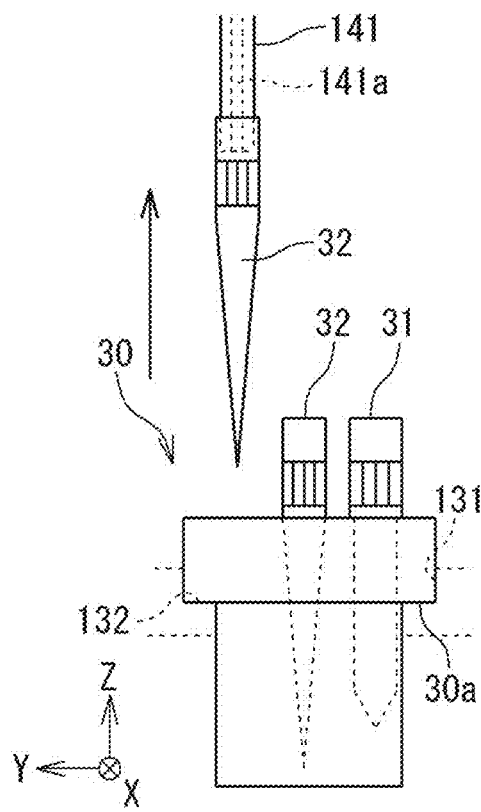
Figure 3:
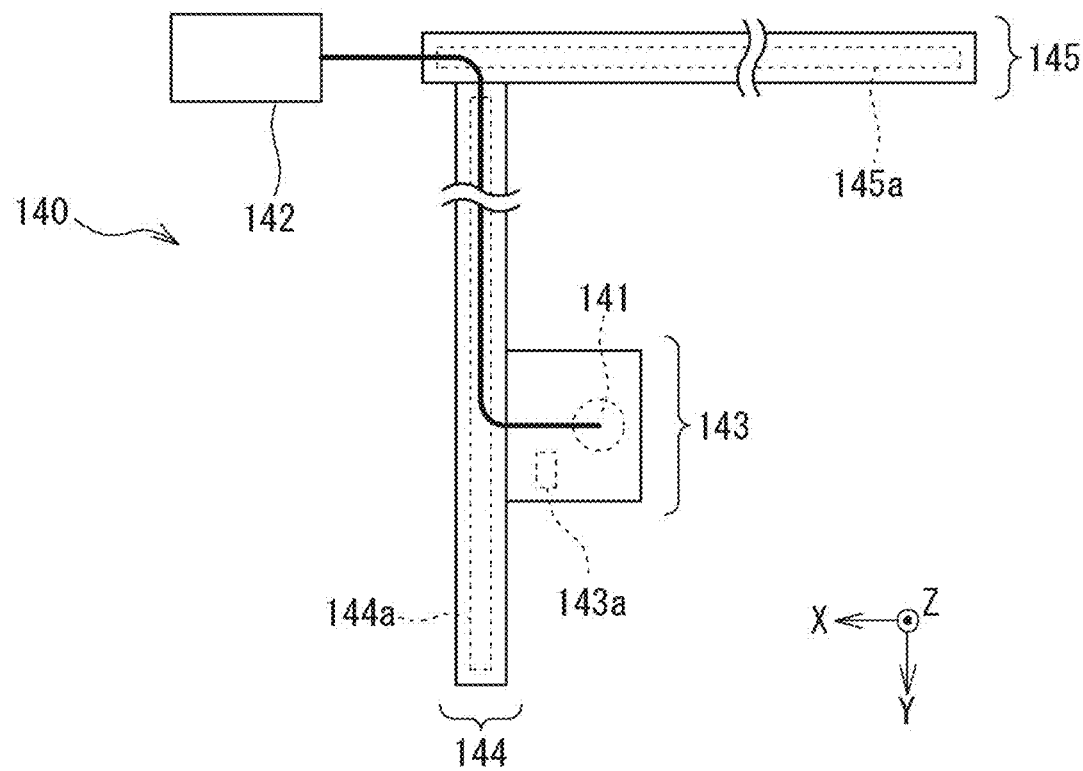

In the fourth simulation, the shear stress distribution and the shear stress maximum value over time were obtained by setting the discharge position to be different in the X-axis direction in FIG. 1 and FIG. 3. In the fourth simulation, $\theta=20°$ and R=1.75 mm, and the other simulation conditions were the same as in the first simulation.

Figure 26:
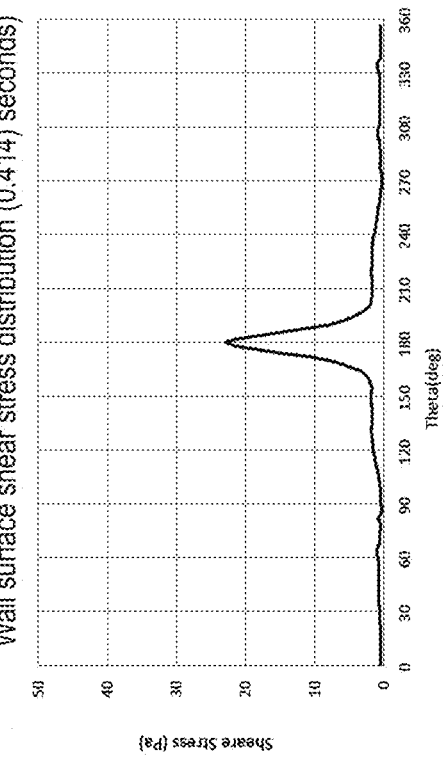
FIGS. 26A through 26D are shear stress distribution charts and shear stress maximum value transition charts.
Figure 26:
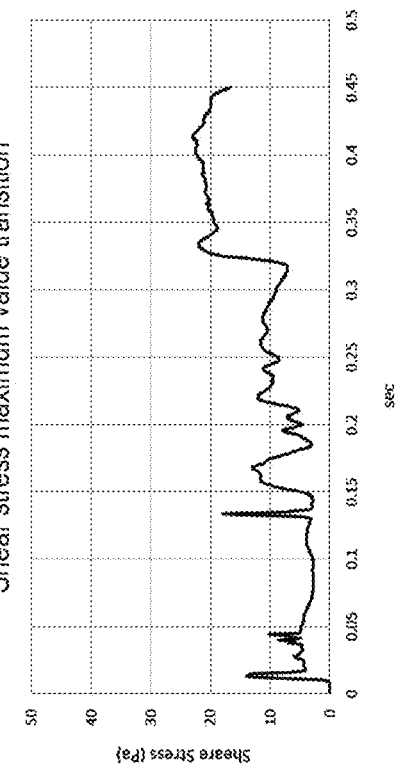
Figure 26:
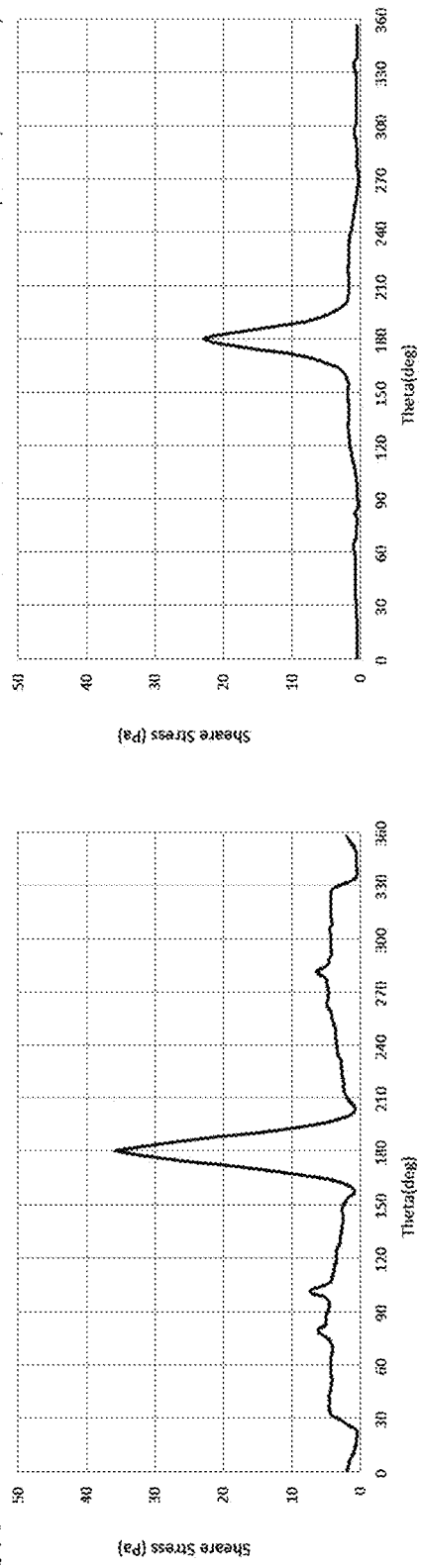
Figure 26:
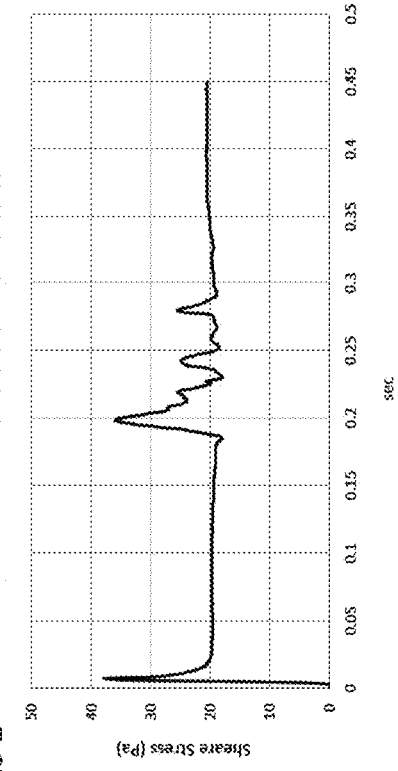

FIG. 26 shows a case in which the position at the distance X=1.2 mm from the central axis 300 was set as the discharge position. FIG. 26A shows the shear stress distribution for the tapered bottom container 12, and FIG. 26B shows the change over time in the shear stress maximum value. FIG. 26C is a cross-sectional view of the shear stress distribution of the ellipsoidal bottom container 212, and FIG. 26D shows the change over time of the maximum value of shear stress for the ellipsoidal bottom container 212.

FIG. 27 shows a case in which a position at a distance X=1.5 mm from the central axis 300 was set as the discharge position. FIG. 27A shows the shear stress distribution for the tapered bottom container 12, and FIG. 27B shows the change over time in the shear stress maximum value. FIG. 27C shows the shear stress distribution for the ellipsoidal bottom container 212, and FIG. 27D shows the change over time of the shear stress maximum value for the ellipsoidal bottom container 212.

Figure 28:
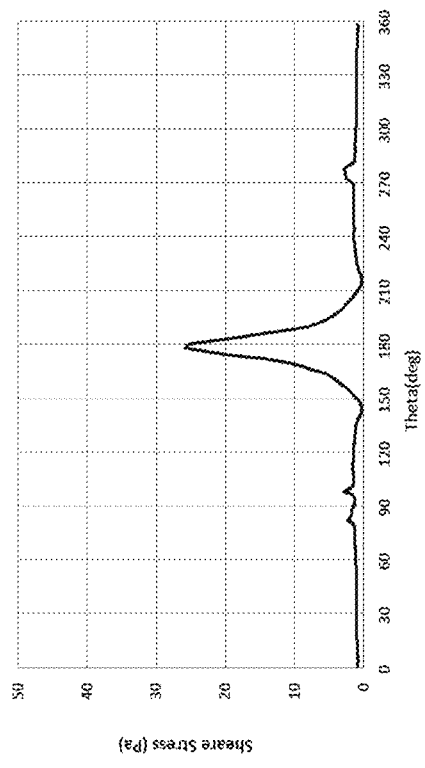
FIGS. 28A through 28D are shear stress distribution charts and shear stress maximum value transition charts.
Figure 28:
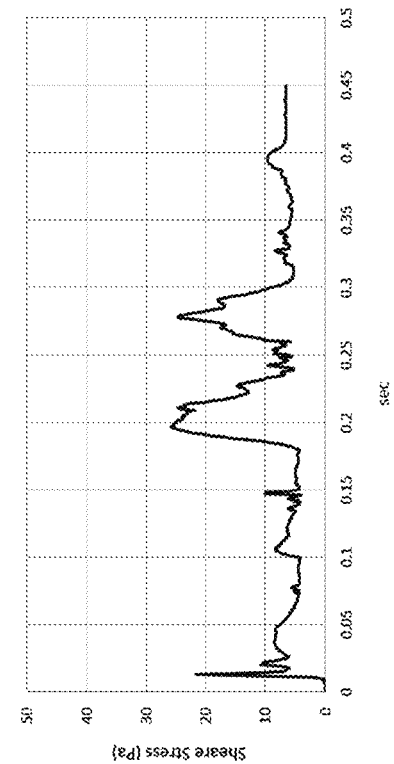
Figure 28:
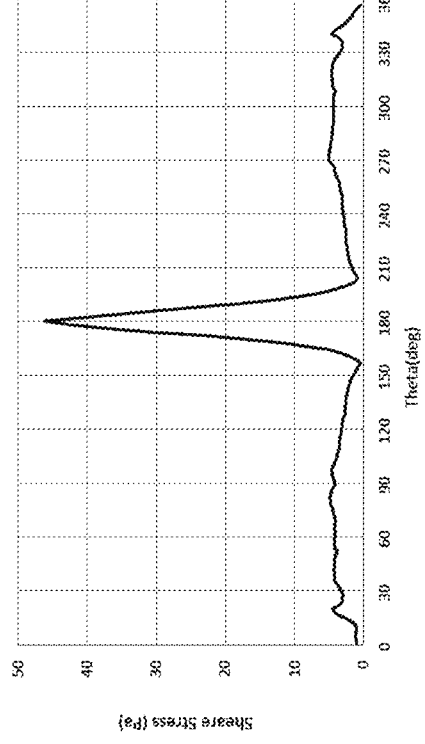
Figure 28:
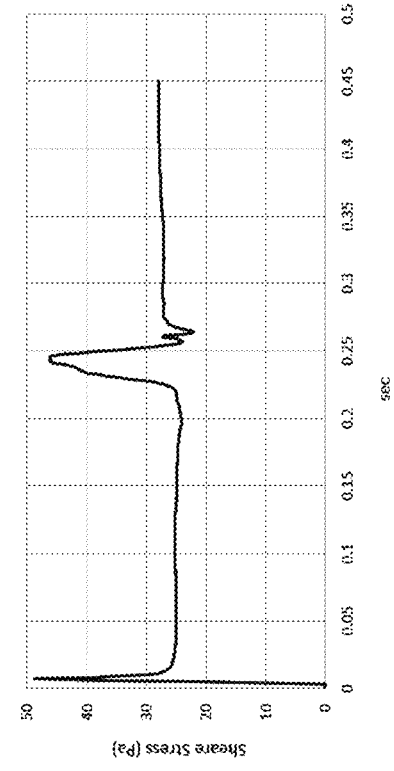

FIG. 28 shows the case in which a position at a distance X=1.8 mm from the central axis 300 was set as the discharge position. FIG. 28A shows the shear stress distribution for the tapered bottom container 12, and FIG. 28B shows the change over time in the shear stress maximum value. FIG. 28C shows the shear stress distribution of the ellipsoidal bottom container 212, and FIG. 28D shows the change over time of the shear stress maximum value for the ellipsoidal bottom container 212.

According to FIG. 26 to FIG. 28, the tapered bottom container 12 is superior to the ellipsoidal bottom container 212 from the perspectives of the magnitude of the shear stress and directivity as well as the stability of the maximum value of the shear stress over time at any of the discharge positions. Particularly good results are obtained when X is 1.5 mm or 1.8 mm in the tapered bottom container 12.

What is claimed is:

1. A particle dispersion method for dispersing magnetic particles in a liquid, the method comprising:
   step of accommodating the magnetic particles in a reaction tank having a cylindrical main body part and an inclined part, wherein a top portion of the inclined part is connected to a bottom portion of the cylindrical main body part, and wherein an inner diameter of the inclined part decreases from the top portion of the inclined part to a bottom portion of the inclined part;
   step of forming an aggregation of the magnetic particles in the liquid on a first side of the inclined part; and
   step of discharging, by a nozzle provided within a predetermined distance above a second side of the inclined part, the liquid toward a second side of the inclined part from above the inclined part, the second side of the inclined part being symmetrical to the first side of the inclined part around a central axis of the reaction tank, wherein a flow of the liquid running from the second side to the first side is generated to disperse the magnetic particles in the aggregation.

2. The particle dispersion method according to claim 1, further comprising:
   step of suctioning the liquid in the reaction tank;
   wherein the discharge step is performed after the suction step.

3. The particle dispersion method according to claim 2, wherein
   in the suction step, suctioning of the liquid is performed until the magnetic particles attached to an inner surface of the first side of the inclined part are exposed from the liquid surface of the liquid.

4. The particle dispersion method according to claim 1, further comprising:
   after the discharge step, a second discharge step of suctioning the liquid in the reaction tank and then, discharging the liquid at a second discharge position different from a discharge position of a prior discharge step in the second side of the inclined part.

5. The particle dispersion method according to claim 4, wherein
   the discharge position in the discharge step and the second discharge position in the second discharge step are different in the circumferential direction of the reaction tank.

6. The particle dispersion method according to claim 2, wherein
   the discharge position in the discharge step is above the suction position in the suction step.

7. The particle dispersion method according to claim 2, wherein
   in the suction step, suction of the liquid is performed on the central axis of the reaction tank.

8. The particle dispersion method according to claim 2, wherein
   in the suction step, the liquid is suctioned in the second side of the inclined part.

9. The particle dispersion method according to claim 1, wherein
   the discharge position in the discharge step is a position at which a tip of the nozzle that discharges a liquid is immersed in the discharged liquid.

10. The particle dispersion method according to claim 1, wherein
    the reaction tank further comprises a bottom part having a rounded shape.

11. The particle dispersion method according to claim 10, wherein
    the roundness of the bottom part is such that a radius of curvature of a circle contacting an arbitrary point in the roundness is 1 mm or more and 3 mm or less.

12. The particle dispersion method according to claim 10, wherein
    the roundness of the bottom part is such that a radius of curvature of a circle contacting an arbitrary point in the roundness is 1 mm or more and 3 mm or less.

13. The particle dispersion method according to claim 1, wherein
    the angle of the inclined part relative to the central axis of the reaction tank is 5° or more and 60° or less.

14. The particle dispersion method according to claim 1, wherein
    the angle of the inclined part relative to the central axis of the reaction tank is 10° or more and 45° or less.

15. The particle dispersion method according to claim 1, wherein the magnetic particles have attached nucleic acid.

16. The particle dispersion method according to claim 1, wherein the magnetic particles having attached nucleic acid are aggregated by magnetic force.

17. The particle dispersion method according to claim 1, wherein
the liquid includes an organic solvent.

* * * * *

UNITED STATES PATENT AND TRADEMARK OFFICE
CERTIFICATE OF CORRECTION

| | |
|---|---|
| PATENT NO. | : 11,169,057 B2 |
| APPLICATION NO. | : 15/825992 |
| DATED | : November 9, 2021 |
| INVENTOR(S) | : Tobimatsu et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 430 days.

Signed and Sealed this
Seventh Day of February, 2023

Katherine Kelly Vidal
*Director of the United States Patent and Trademark Office*